(12) United States Patent
Briscoe et al.

(10) Patent No.: US 7,168,265 B2
(45) Date of Patent: Jan. 30, 2007

(54) INTEGRATED PROCESSING OF NATURAL GAS INTO LIQUID PRODUCTS

(75) Inventors: Michael D. Briscoe, Katy, TX (US); Theo H. Fleisch, Houston, TX (US); Michael J. Gradassi, Houston, TX (US); Jeffrey H. Sawchuk, Houston, TX (US); Pedro Ernesto Fischer-Calderon, Missouri City, TX (US)

(73) Assignee: BP Corporation North America Inc., Warrenville, IL (US)

( * ) Notice: Subject to any disclaimer, the term of this patent is extended or adjusted under 35 U.S.C. 154(b) by 358 days.

(21) Appl. No.: 10/805,982

(22) Filed: Mar. 22, 2004

(65) Prior Publication Data

US 2004/0248999 A1 Dec. 9, 2004

Related U.S. Application Data

(60) Provisional application No. 60/458,005, filed on Mar. 27, 2003.

(51) Int. Cl.
*F25J 1/00* (2006.01)
*C07C 27/00* (2006.01)
*C07C 27/06* (2006.01)

(52) U.S. Cl. .................. 62/611; 518/705; 518/700; 62/613

(58) Field of Classification Search .......... 62/611, 62/613; 518/700, 702, 703, 705, 706
See application file for complete search history.

(56) References Cited

U.S. PATENT DOCUMENTS

| | | | |
|---|---|---|---|
| 2,609,382 A | 9/1952 | Mayland | |
| 2,814,936 A | 12/1957 | Morrison | |
| 3,331,214 A | 7/1967 | Proctor et al. | |
| 3,360,944 A | 1/1968 | Knapp et al. | |
| 3,373,574 A | 3/1968 | Fisher | |
| 3,433,026 A | 3/1969 | Swearingen | |
| 3,616,652 A | 11/1971 | Engel | |
| 3,721,009 A | 3/1973 | Lucich | |
| 4,195,979 A | 4/1980 | Martin | |
| 4,430,103 A | 2/1984 | Gray et al. | |
| 4,445,917 A | 5/1984 | Chiu | |
| 4,559,069 A | 12/1985 | Becker | |
| 4,638,638 A | 1/1987 | Marshall et al. | |

(Continued)

FOREIGN PATENT DOCUMENTS

DE 19821242 11/1999

(Continued)

OTHER PUBLICATIONS

U.S. Appl. No. 10/805,943, filed Mar. 22, 2004.

(Continued)

*Primary Examiner*—William C. Doerrler
(74) *Attorney, Agent, or Firm*—John L. Wood

(57) ABSTRACT

An integrated process for producing LNG and GTL products is provided, wherein a $CO_2$-containing natural gas feed to an LNG production zone is first pre-treated to separate at least a portion of the $CO_2$ therefrom, and the resulting $CO_2$ stream obtained thereby is then directed to a GTL production zone and utilized to make GTL products that include methanol and/or methanol derivatives.

46 Claims, 5 Drawing Sheets

U.S. PATENT DOCUMENTS

| | | | | |
|---|---|---|---|---|
| 5,537,827 | A * | 7/1996 | Low et al. | 62/613 |
| 5,733,941 | A | 3/1998 | Waycuilis | |
| 5,755,114 | A | 5/1998 | Foglietta | |
| 6,011,073 | A | 1/2000 | Agee et al. | |
| 6,023,942 | A | 2/2000 | Thomas et al. | |
| 6,041,619 | A | 3/2000 | Fischer et al. | |
| 6,062,041 | A | 5/2000 | Kikkawa et al. | |
| 6,105,390 | A * | 8/2000 | Bingham et al. | 62/613 |
| 6,159,395 | A * | 12/2000 | Early et al. | 252/372 |
| 6,180,684 | B1 | 1/2001 | Halmo et al. | |
| 6,248,794 | B1 | 6/2001 | Gieskes | |
| 6,258,860 | B1 * | 7/2001 | Weedon et al. | 518/706 |
| 6,289,692 | B1 | 9/2001 | Houser et al. | |
| 6,449,984 | B1 | 9/2002 | Paradowski | |
| 6,564,578 | B1 | 5/2003 | Fischer-Calderon | |
| 6,743,829 | B2 | 6/2004 | Fischer-Calderon et al. | |
| 2004/0242707 | A1 * | 12/2004 | De Graaf et al. | 518/702 |

FOREIGN PATENT DOCUMENTS

| | | |
|---|---|---|
| EP | 0178007 | 4/1986 |
| EP | 1273860 | 1/2003 |
| GB | 2357140 | 6/2001 |
| WO | 9836038 | 8/1998 |
| WO | 9930094 | 6/1999 |
| WO | 9941217 | 8/1999 |
| WO | 9958917 | 11/1999 |
| WO | 0362724 | 7/2003 |

OTHER PUBLICATIONS

Pruitt, "Mineral Terms—Some Problems In Their Use and Definition," Rocky Mt. Min. L. Rev. 1, 16 (1966).

Geisel, et al., "Synergies Between LNG and GTL Conversion", 13th Int'l Conf. & Exhibition on LNG, Seoul, Korea.

Kick-Othmer Encyclopedia of Chemical Technology, vol. 16, pp. 537-556 (4th Ed. 1995).

Brown, et al., "Integration of GTL Plants with Adjacent LNG Complex", Research Disclosure Kenneth Mason Publications vol. 467, No. 32 (Mar. 2003).

Search Report & Written Opinion PCT/US2004//008779.

* cited by examiner

INTEGRATED PROCESSING OF NATURAL GAS INTO LIQUID PRODUCTS

CROSS REFERENCE TO RELATED APPLICATIONS

This application claims benefit of U.S. Provisional Application Ser. No. 60/458,005, filed Mar. 27, 2003, the teachings of which are incorporated herein by reference in their entirety.

Filed concurrently on even date herewith is the application entitled "Fuel Compositions Comprising Natural Gas and Dimethyl Ether and Methods For Preparation of the Same", which claims benefit from U.S. Provisional Application Ser. No. 60/458,213, filed Mar. 27, 2003. The teachings of both applications are also incorporated herein by reference.

FIELD OF THE INVENTION

The present invention relates to a process for producing commercial products from natural gas. More particularly, this invention relates to an integrated process for producing liquefied natural gas and products made through natural gas conversion technology, such as methanol and its chemical derivatives.

BACKGROUND OF THE INVENTION

Natural gas generally refers to rarefied or gaseous hydrocarbons (methane and higher hydrocarbons such as ethane, propane, butane, and the like) which are found in the earth. Non-combustible gases occurring in the earth, such as carbon dioxide, helium and nitrogen are generally referred to by their proper chemical names. Often, however, non-combustible gases are found in combination with combustible gases and the mixture is referred to generally as "natural gas" without any attempt to distinguish between combustible and non-combustible gases. See Pruitt, "Mineral Terms-Some Problems in Their Use and Definition," Rocky Mt. Min. L. Rev. 1, 16 (1966).

Natural gas is often plentiful in regions where it is uneconomical to develop the reserves due to lack of a local market for the gas or the high cost of processing and transporting the gas to distant markets.

It is common practice to cryogenically liquefy natural gas so as to produce liquefied natural gas (LNG) for storage and transport. A fundamental reason for the liquefaction of natural gas is that liquefaction results in a volume reduction of about 1/600, thereby making it possible to store and transport the liquefied gas in containers at low or even atmospheric pressure. Liquefaction of natural gas is of even greater importance in enabling the transport of gas from a supply source to market where the source and market are separated by great distances and pipeline transport is not practical or economically feasible.

In order to store and transport natural gas in the liquid state, the natural gas is preferably cooled to −240° F. (−151° C.) to −260° F. (−162° C.) where it may exist as a liquid at near atmospheric pressure. Various methods and/or systems exist in the prior art for liquefying natural gas or the like whereby the gas is liquefied by sequentially passing the gas at an elevated pressure through a plurality of cooling stages, and cooling the gas to successively lower temperatures until liquefaction is achieved. Cooling is generally accomplished by heat exchange with one or more refrigerants such as propane, propylene, ethane, ethylene, nitrogen and methane, or mixtures thereof. The refrigerants are commonly arranged in a cascaded manner, in order of diminishing refrigerant boiling point. For example, processes for preparation of LNG generally are disclosed in U.S. Pat. Nos. 4,445,917; 5,537,827; 6,023,942; 6,041,619; 6,062,041; 6,248,794, and UK Patent Application GB 2,357,140 A. The teachings of these patents are incorporated herein by reference in their entirety.

Additionally, chilled, pressurized natural gas can be expanded to atmospheric pressure by passing the natural gas through one or more expansion stages. During the course of this expansion to atmospheric pressure, the gas is further cooled to a suitable storage or transport temperature by flash vaporizing at least a portion of the already liquefied natural gas. The flashed vapors from the expansion stages are generally collected and recycled for liquefaction or burned to generate power for the LNG manufacturing facility.

LNG projects have not always been economical in that cryogenic refrigeration systems are highly energy intensive and require a substantial capital investment. In addition, participating in the LNG business requires further investment for sophisticated and costly shipping vessels and regasification systems so that the LNG consumer can process the product.

An alternative to the cryogenic liquefaction of natural gas to LNG is the chemical conversion of natural gas into GTL (GTL) products. Methods for producing GTL products can be conveniently categorized as indirect synthesis gas routes or as direct routes. The indirect synthesis gas routes involve the production of synthesis gas comprising hydrogen and carbon dioxide as an intermediate product whereas, for purposes of the present invention, the direct routes shall be construed as covering all others.

Traditional GTL products include, but are not limited to, hydrogen, methanol, acetic acid, olefins, dimethyl ether, dimethoxy methane, polydimethoxy methane, urea, ammonia, fertilizer and Fischer Tropsch reaction products. The Fischer Tropsch reaction produces mostly paraffinic products of varying carbon chain length, useful for producing lower boiling alkanes, naphtha, distillates useful as jet and diesel fuel and furnace oil, and lubricating oil and wax base stocks.

The most common commercial methods for producing synthesis gas are steam-methane reforming, auto-thermal reforming, gas heated reforming, partial oxidation, and combinations thereof.

Steam methane reforming generally reacts steam and natural gas at high temperatures and moderate pressures over a reduced nickel-containing catalyst to produce synthesis gas.

Autothermal reforming generally processes steam, natural gas and oxygen through a specialized burner where only a portion of the methane from the natural gas is combusted. Partial combustion of the natural gas provides the heat necessary to conduct the reforming reactions that will occur over a catalyst bed located in proximity to the burner.

Gas heated reforming consists of two reactors or reaction zones, a gas heated reformer reactor/zone and an autothermal reformer reactor/zone. Steam and natural gas are fed to the gas-heated reformer where a portion of the natural gas reacts, over catalyst, to form synthesis gas. This mixture of unreacted natural gas and synthesis gas is then fed to the autothermal reformer, along with oxygen, where the remaining natural gas is converted to synthesis gas. The hot synthesis gas stream exiting the autothermal reformer is then routed back to the gas reformer to provide the heat of reaction necessary for the gas-heated reformer.

Partial oxidation reforming generally processes steam, natural gas and oxygen through a specialized burner where a substantial portion of the methane is combusted at high temperatures to produce synthesis gas. Contrary to autothermal reforming, no catalyst is present in the partial oxidation reactor.

Current technology for manufacturing synthesis gas is highly capital intensive. Autothermal and partial oxidative synthesis gas methods generally require a costly air separation plant to produce oxygen. Steam methane reforming on the other hand, does not require oxygen manufacture.

Natural gas reserve holders have found that substantially increasing the capacity of a LNG or GTL plant can improve plant construction economics. Many of the costs inherent to building such plants are fixed or minimally, do not increase linearly with capacity. However, it has also been found that as more of a single product is produced in a distinct and often isolated geographical region, the product price over cost margin for blocks of product if not all of the plant output is reduced.

Integrating a LNG plant and a GTL plant offers the potential for producing a portfolio of products which can turn projects that would not have been commercially viable for many of the above noted reasons into viable projects. While it is believed that there have been no integrated LNG/GTL plants built to date, there has been increased interest in combining both technologies at a single plant site.

For example, Geijsel et al., "Synergies Between LNG and GTL Conversion," The 13th International Conference & Exhibition on Liquefied Natural Gas, Seoul, Korea, May 14–17, discloses potential benefits for combining a Fischer Tropsch GTL plant (utilizing a combined partial oxidation/steam reforming synthesis gas preparation step) with LNG manufacture.

U.S. Pat. No. 6,248,794 to Gieskes similarly discloses a method for utilizing tail gas from a Fischer Tropsch GTL plant as fuel for a refrigeration plant at an LNG facility.

Commonly assigned co-pending U.S. patent application Ser. No. 10/051,425, filed Jan. 18, 2002, discloses a method for utilizing flash gas from an LNG process as feed for a GTL process making GTL products. The teachings of this application are incorporated by reference herein in their entirety.

The above-referenced teachings in the area of integrated LNG with GTL technology are largely directed to the sharing of common plant infrastructure and utilities and other incremental consolidation improvements.

U.K. Patent Application GB 2357140 to Rummelhoff is directed to a process for integrating natural gas liquids (NGL) recovery, LNG production and methanol manufacture. The Rummelhoff process performs two expansion and separation steps so as to provide energy recovery sufficient to facilitate the separation of higher boiling natural gas liquids ("NGLs") such as ethane and higher boiling point hydrocarbon) from LNG. Subsequent to NGL recovery, the Rummelhoff process provides a single, final stage of expanding and separating so as to remove a natural gas stream from LNG for conveying to post-processing steps such as the production of methanol.

U.S. Pat. No. 6,180,684 to Halmo et al. discloses integrating the production of synthetic fuel and electrical power generation. While the process disclosed therein provides for separation of acid gases, such as $CO_2$, from a feed stream directed to LNG production, the $CO_2$ obtained thereby is subsequently directed to reforming processes which require oxygen to prepare synthesis gas.

At present, commercial scale LNG plants use processes which generally require nearly complete removal of acid gases, including $CO_2$, from the feed gas. In the past, the $CO_2$ extracted from the feed gas has been simply vented to the atmosphere. However, current concerns over global warming, internationally-driven initiatives to reduce greenhouse emissions, and other environmental factors make venting of such $CO_2$ undesirable.

SUMMARY OF THE INVENTION

The present invention is directed to more effectively integrating the LNG and GTL phases and processing steps of an integrated process, and also provides an alternative to venting of $CO_2$ into the atmosphere in connection with production of LNG.

Therefore, in one aspect, the present invention is directed to an integrated process for producing LNG products in a LNG Phase production zone and GTL products that include methanol in a GTL Phase production zone from a natural gas comprising hydrocarbons and $CO_2$. The process comprises the steps of:

pre-treating at least a first portion of the natural gas to separate at least a portion of the $CO_2$ therefrom and produce a natural gas feed having reduced $CO_2$ content and a stream rich in $CO_2$;

converting the natural gas feed into an LNG product in the LNG Phase;

converting a second portion of the natural gas to a synthesis gas by steam methane reformation; and reacting the stream rich in $CO_2$ with at least a portion of the synthesis gas in the GTL Phase to produce methanol.

In another aspect, the invention is directed to an integrated process for producing LNG products in a LNG Phase production zone and GTL products that include methanol in a GTL Phase production zone from a natural gas comprising hydrocarbons and $CO_2$. The process comprises the steps of:

pre-treating at least a first portion of the natural gas to separate at least a portion of the $CO_2$ therefrom and produce a natural gas feed having reduced $CO_2$ content and a stream rich in $CO_2$;

converting the natural gas feed into at least one natural gas vapor component and an LNG product in the LNG Phase;

converting the at least one natural gas vapor component, and optionally a second portion of the natural gas, to a synthesis gas by steam methane reformation; and reacting the stream rich in $CO_2$ with at least a portion of the synthesis gas in the GTL Phase to produce methanol.

In addition, in other optional embodiments further desirable integration benefits can be obtained by combining the foregoing $CO_2$ utilization feature with performing in an LNG process at least two expansion and separation cycles subsequent to substantial removal of NGLs from a cooled natural gas stream during LNG production, as this can provide substantial integration benefits over processes limited to a single expansion and separation step constrained to processing conditions necessary to produce a final LNG product.

In other embodiments, it has also been found that directing an expanded natural gas vapor for GTL conversion, available at more favorable conditions of pressure and temperature, from such higher pressure expansion and separation steps, provides substantial energy and capital savings compared to processes which require separate facilities for compressing and heating a natural gas vapor present at near atmospheric pressure and substantially colder temperatures.

In other embodiments, it has also been found that performing at least two expansion and separation cycles subsequent to substantial removal of NGLs from a cooled natural gas stream permits the plant operator to customize and improve the quality of the LNG product produced compared to LNG product produced from a single expansion and separation cycle constrained to a final atmospheric LNG separation step.

The fully integrated process of the present invention provides substantial benefits over teachings in the art directed to the sharing of common plant infrastructure and utilities and processes reliant on a single expansion and separation step for producing LNG.

The present invention provides a more effective integration of the LNG and GTL phases and their related processing steps, as it utilizes a relatively low value $CO_2$ vent stream to produce products having higher value, such as methanol and its related derivatives, and the invention also provides a more environmentally acceptable alternative to venting of waste $CO_2$ into the atmosphere in connection with production of LNG.

The present invention further provides an integrated process for producing LNG and GTL products that effectively shifts non-combustibles such as nitrogen and helium, from the LNG Phase and LNG product to the GTL Phase and GTL feed where it can be effectively processed.

The present invention in embodiments also provides an integrated process for producing LNG and GTL products that synergistically permits a substantial portion of cooled natural gas vapor or LNG component to be isentropically or isenthalpically expanded and directed to the GTL Phase for conversion to GTL products foregoing the need to recompress and refrigerate such material for reinjection back into the LNG refrigeration system or to reject such stream to fuel. At the same time, the isentropic or isenthalpic expansion autorefrigerates and cools the separated residual LNG component thereby providing a synergistic LNG cooling effect reducing the need for supplementary or external refrigeration.

The present invention in embodiments provides an integrated process for producing LNG and GTL products that facilitates the production of a LNG product containing a higher total mole percentage of ethane and higher boiling point hydrocarbon and therefore a higher energy content. As another synergistic benefit to the foregoing, removing ethane and higher boiling point hydrocarbon from the GTL Phase feedstock and incrementally directing this material to LNG product is beneficial in that lower concentrations of ethane and higher boiling point hydrocarbon in the GTL Phase feedstock reduces pre-reforming requirements even to the point of eliminating the pre-reforming step entirely.

The process of the present invention in embodiments provides an integrated process for producing LNG and GTL products that synergistically and more efficiently utilizes available natural gas pressure while at the same time minimizes compressor capital and/or energy requirements.

DETAILED DESCRIPTION OF THE INVENTION

Figure 1:
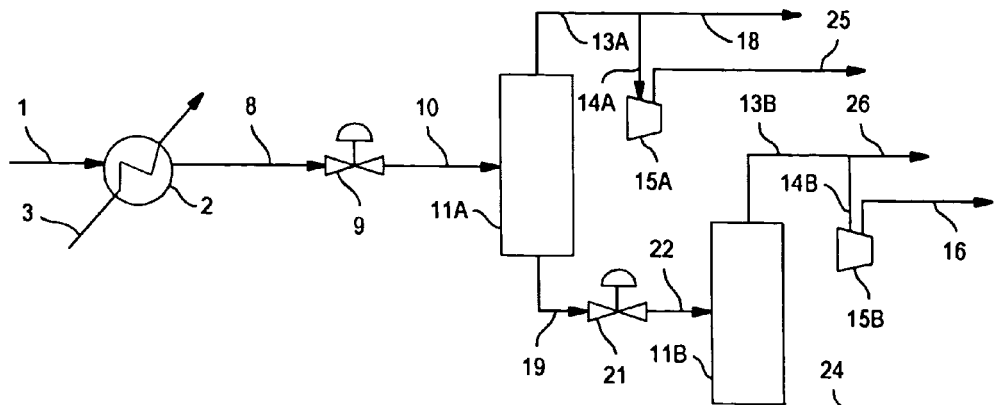
FIG. 1 is directed to an integrated process for producing LNG and GTL products which includes a first isenthalpic or isentropic expansion, followed by a separation step for producing a first LNG component, followed by a second isenthalpic or isentropic expansion and a second separation step for providing a further enhanced LNG product and multiple natural gas vapor streams available at multiple pressures for directing for GTL conversion.

The present invention is directed to an integrated process for producing LNG and GTL products from natural gas as that term is defined above. The natural gas contemplated herein generally comprises at least 50 mole percent methane, preferably at least 75 mole percent methane, and more preferably at least 90 mole percent methane for best results. The balance of natural gas generally comprises other combustible hydrocarbon such as, but not limited to, lesser amounts of ethane, propane, butane, pentane, and heavier hydrocarbons and non-combustible components such as carbon dioxide, hydrogen sulfide, helium and nitrogen.

The presence of heavier hydrocarbons such as ethane, propane, butane, pentane, and hydrocarbon boiling at a boiling point above propane is generally reduced in the natural gas through gas-liquid separation steps. Hydrocarbon boiling at a temperature above the boiling point of pentane or hexane is generally directed to crude oil. Hydrocarbon boiling substantially at a temperature above the boiling point of ethane and below the boiling point of pentane or hexane is generally removed and considered to be natural gas liquids or "NGLs" for purposes of the present invention.

The natural gas processed in accordance with the processing steps of the present invention is preferably of a composition such that it may be directed for the manufacture of LNG or GTL products without requiring additional processing steps for removal of NGLs.

For most markets, it is also desirable to minimize the presence of non-combustibles and contaminants in LNG such as carbon dioxide, helium and nitrogen and hydrogen sulfide. Depending on the quality of a given natural gas reservoir (which may contain as much as 50% to 70% carbon dioxide), the natural gas may be pre-processed at a natural gas plant for pre-removal of such of the above components or may be conveyed directly to the integrated plant for pre-processing prior to manufacture of LNG and GTL products. A feature of the invention herein is the utilization of carbon dioxide within the natural gas as a means for integration of the LNG process with a GTL process, wherein the $CO_2$ is employed to produce methanol generally by known synthesis methods, and the methanol so-produced may be further converted by known methods into any of a wide variety of methanol derivatives, such as dimethyl ether, acetic acid, formaldehyde, and olefins. Accordingly, the natural gas feed to the LNG phase is pre-treated, prior to liquefaction in the LNG phase, to separate the $CO_2$ therein for use in the GTL phase as described hereinafter.

A preferred LNG product, in accordance with the present invention, generally comprises:

less than 2 mole percent nitrogen and preferably less than 1 mole percent nitrogen;

less than 1 mole percent and preferably less than 0.5 mole percent helium;

less than 3 mole percent and preferably less than 1.5 mole percent of the total of nitrogen and helium; and less than 12 mole percent of ethane and higher boiling point hydrocarbon, and preferably less than 4 mole percent ethane and higher boiling point hydrocarbon.

A typical gross heating value for LNG produced in accordance with the present invention generally ranges from about 1000 Btu/scf to about 1200 Btu/scf and more preferably from about 1000 Btu/scf to about 1100 Btu/scf. However, with larger amounts of ethane and higher hydrocarbons left and/or added therein, the gross heating value for LNG product can have an enhanced heating value such as up to about 1500 Btu/scf, and more typically from about 1200 Btu/scf to about 1400 Btu/scf.

Depending on the geographic market place, the process of the present invention can be utilized to synergistically enhance the heating value of the LNG by concentrating a sufficient amount of ethane and higher boiling point hydrocarbon in the LNG product. LNG produced in such an embodiment of the present invention can realize an increase in gross heating value of about 7.7 Btu/scf for each mole percent increase in ethane concentration over methane; 15.2 Btu/scf for each mole percent increase in propane concentration over methane; and 22.5 Btu/scf for each mole percent increase in butane concentration over methane. It has also been found that a LNG product produced in accordance with the present invention can realize an increase in gross heating value of about 11 Btu/scf for each mole percent increase in methane over non-combustibles.

Natural gas is generally made available or transported at pressures as high as 2800 psig, more commonly at pressures ranging from 100 psig to 1400 psig, and most commonly at pressures ranging from 400 psig to 1200 psig. The temperature of the natural gas is dependent on its originating source. Where the natural gas is pipeline gas, its temperature can approximate ambient conditions such as for example, 0° F. to 120° F. If the natural gas conditions are measured in proximity to a conveyance device such as a natural gas compressor, outlet and post-compression equipment may dictate or affect the temperature and pressure of the natural gas feed.

Pretreatment steps suitable for use with the present invention generally begin with steps commonly identified and known in connection with LNG or GTL production, including, but not limited to, removal of acid gases (such as $H_2S$ and $CO_2$), mercaptans, mercury and moisture from the natural gas stream. Acid gases and mercaptans are commonly removed via a sorption process employing an aqueous amine-containing solution or other types of known physical or chemical solvents. This step is generally performed upstream of most of the natural gas cooling steps. A substantial portion of the water is generally removed as a liquid through two-phase gas-liquid separation prior to or after low level cooling, followed by molecular sieve processing for removal of trace amounts of water. The water removal steps generally occur upstream of any isenthalpic or isentropic expansion as contemplated herein. Mercury is removed through use of mercury sorbent beds. Residual amounts of water and acid gases are most commonly removed through the use of particularly selected sorbent beds such as regenerable molecular sieves. Such particularly selected sorbent beds are also generally positioned upstream of most of the natural gas cooling steps. Preferably, the pretreatment of the natural gas results in a natural gas feed to the LNG Phase having a $CO_2$ content of less than 0.1 mole percent, and more preferably less than 0.01 mole percent, based on the total feed. In accordance with the invention, it is desirable to prepare a $CO_2$ rich stream for use in the GTL Phase of the process, wherein the $CO_2$ rich stream has minimal amounts of other contaminants therein, such as H2S, mercaptans, and other sulfur-containing compounds.

As known in the art, an inhibited amine solution can be used to selectively remove the $CO_2$ in the natural gas stream, but not $H_2S$. The $H_2S$ can then be removed in a subsequent step. Also, it is desirable to employ a guard bed (such as a ZnO guard bed) for removal of any remaining, residual sulfur-containing compounds in the $CO_2$ rich stream prior to feeding the stream to points within the GTL Phase, such as upstream of a pre-reforming reactor or reforming reactor. Such reactors typically employ nickel catalysts which are susceptible to poisoning by sulfur-containing compounds, such as $H_2S$.

It has been found that full integration of the LNG and GTL concepts in accordance with the present invention may, in some embodiments, also realize a synergistic benefit from a water removal step. It has been found that substantially reducing the water content of the natural gas prior to at least one isenthalpic or isentropic expansion steps as mentioned hereinafter can result in a GTL feed stream comprising substantially less water. The lower water concentration of the natural gas feeding the GTL processing steps results in a substantial improvement in control of the hydrogen to carbon monoxide ratio of the synthesis gas. Maintaining a particular synthesis gas stoichiometric ratio of hydrogen to carbon monoxide is beneficial in order to optimally convert the synthesis gas into salable products. For example, the preferred hydrogen to carbon monoxide ratio is generally higher for conversion of synthesis gas into hydrogen than would be preferred for conversion to Fischer Tropsch products.

LNG Phase of Integrated Process

In general, the LNG Phase employed in the practice of the present invention may comprise any LNG process, and in some embodiments described hereinafter, it is desired to employ a LNG process which produces a flash gas, i.e., a natural gas vapor component, during processing of the natural gas therein. For example, processes for preparation of LNG generally are disclosed in U.S. Pat. Nos. 4,445,917; 5,537,827; 6,023,942; 6,041,619; 6,062,041; 6,248,794, and UK Patent Application GB 2,357,140 A, the teachings of which have been incorporated herein by reference.

Subsequent to the pretreatment steps, the process of the present invention in further embodiments synergistically integrates a GTL process directly with a process for manufacturing LNG. While the invention should be understood as broadly directed toward integrating any LNG process with a GTL process that produces methanol and other GTL products as mentioned hereinafter, it is preferable to employ an LNG process as described hereinafter, wherein hydrocarbon flash gas generated during successive cooling steps within the LNG process is recovered and employed, at least in part, to generate synthesis gas in the GTL process.

In such preferred embodiments, referring now to FIGS. 1 through 5, the pretreated natural gas and/or a combination of pretreated and untreated natural gas 1 is directed to a cooling step 2 or sequence of cooling steps 2 which can include one or more cooling stages targeted to achieve successively lower temperatures. Any suitable refrigerant or combination of refrigerants may be employed as cooling streams 3. For example, because of their availability and cost, preferred refrigerants are ammonia, propane, propylene, ethane, ethylene, methane, and other normally gaseous materials or mixtures thereof which have been compressed and cooled to liquefy the same. The refrigerant may also be incorporated into an open cycle configuration wherein there is intimate contact between the refrigerant and the process stream. To the extent that more than one refrigerant stream is used in the cooling step 2, the refrigerant utilized in the later portion of cooling step 2 will generally have a boiling point lower than the refrigerant utilized in the earlier stages of cooling step 2. In a preferred embodiment, propane is utilized as a first refrigerant and ethane or ethylene is utilized as a subsequent refrigerant. More preferably, propane is utilized as a first refrigerant and ethylene is utilized as a subsequent refrigerant.

Figure 2:
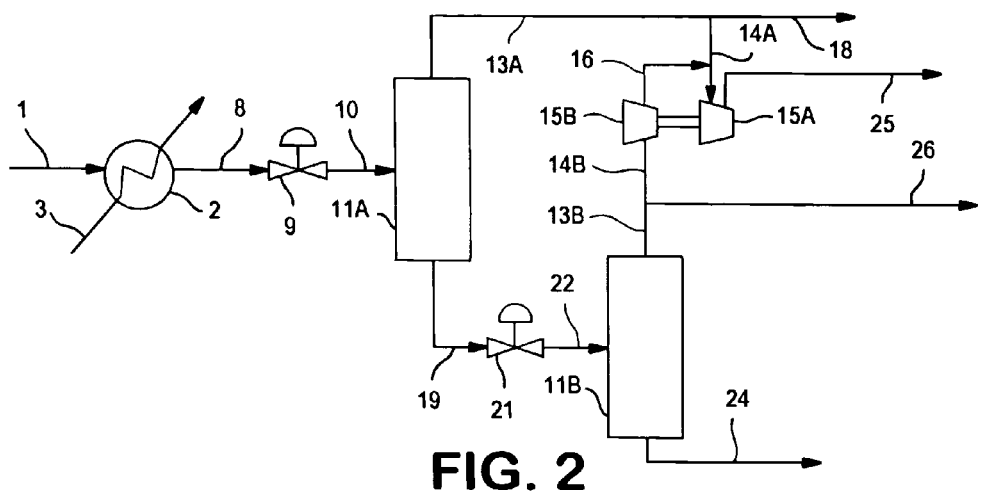
FIG. 2 is directed to an integrated process for producing LNG and GTL products which includes a first isenthalpic or isentropic expansion, followed by a separation step for producing a first LNG component, followed by a second isenthalpic or isentropic expansion and a second separation step wherein the separated natural gas vapor from both separation steps is conveyed to an integrated compression step.

In one embodiment and as described in FIGS. 1 and 2, the cooled natural gas 8 is isentropically or isenthalpically expanded across an expansion device 9 so as to lower the pressure of the natural gas stream 8 and autorefrigerate the natural gas stream to a lower temperature natural gas stream 10.

Suitable devices for isenthalpic expansion of natural gas in accordance with the present invention generally include, but are not limited to, manually or automatically actuated throttling devices such as valves, control valves, Joule Thompson valves, venturi devices, and the like. The preferred isenthalpic expansion devices are automatically actuated control valves or Joule Thompson valves.

Suitable devices for isentropic expansion of natural gas in accordance with the present invention generally include equipment such as expanders or turbo expanders that extract or derive work from such expansion. While the isentropic expansion is depicted, for purposes of FIGS. 1 through 5 in the form of a valve, this depiction shall be construed to comprise the devices contemplated above for both isentropic and isenthalpic expansion.

Isenthalpic or isentropic expansion can be conducted in the all-liquid phase, all-vapor phase, mixed phase or can be conducted so as to facilitate a phase change from liquid to vapor. Isenthalpic or isentropic expansion as contemplated herein can be controlled to maintain a constant pressure drop or temperature reduction across the expansion device, can be operated to maintain LNG product or GTL feed composition properties, or can be operated hydraulically so as to provide sufficient pressure so as to direct flow into a particular downstream use.

Where such an isenthalpic or isentropic expansion is be controlled to a constant pressure drop, suitable pressure drop or reduction ranges will generally extend from about 5 psig to about 800 psig, preferably from about 15 psig to about 650 psig, and more preferably from about 30 psig to about 300 psig for best results. Where the expansion is controlled to a constant temperature reduction, suitable temperature reduction ranges will generally extend from about 0.5° F. to about 150° F., preferably from about 3° F. to about 85° F., and more preferably from about 10° F. to about 50° F. for best results.

Figure 3:
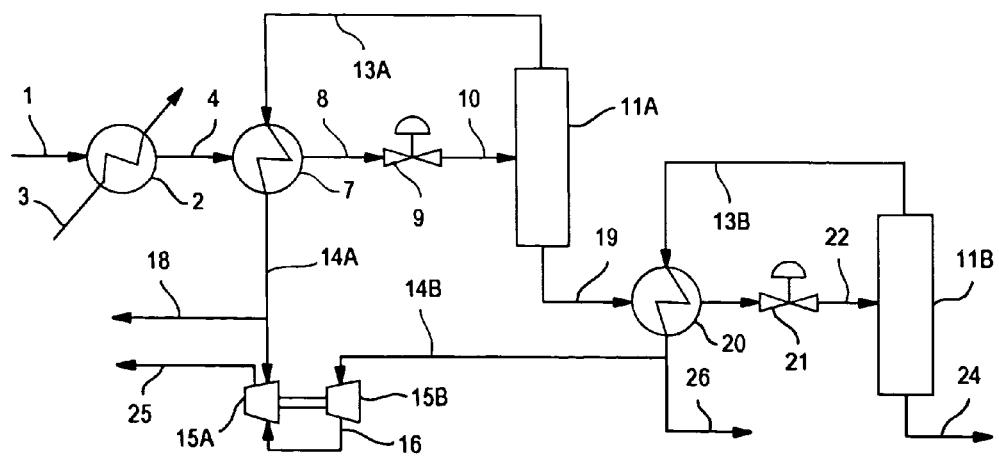
FIG. 3 is directed to an integrated process for producing LNG and GTL products which includes a first isenthalpic or isentropic expansion, followed by a separation step for producing a first LNG component, followed by a second isenthalpic or isentropic expansion and a second separation step wherein the separated natural gas vapor from each separation step is returned to a heat exchange step for precooling the natural gas prior to each respective isenthalpic or isentropic expansion step and wherein the separated natural gas from both separation steps is conveyed to an integrated compression step.

As FIGS. 1 through 3 illustrate, the lower temperature natural gas stream 10 from the isenthalpic or isentropic expansion step is generally directed to a separation device 11A for separating any vaporized natural gas from the liquefied portion of the natural gas.

The liquefied portion of the natural gas, for purposes of the present invention, may also be referred to as the LNG component because it generally has a composition similar to that of the final LNG product but for the possible presence of certain amounts of low-boiling non-combustibles that may be subsequently removed in the process of the present invention. However, the LNG component may not be present at conditions of temperature and pressure so as to exist as a liquid at near atmospheric pressure which traditionally defines LNG or LNG product.

The separation device can be a single stage flash drum or can include multiple theoretical stages of separation for providing better component separation between the constituents in the cooled natural gas vapor components streams 13 and 13A for FIGS. 1 through 5 and the LNG components 19 and 19A for FIGS. 1 through 5. Suitable liquid-gas separation devices for providing multiple theoretical stages of separation can include a distillation tower, which may or may not include a reboiler, a condenser, or reflux.

Depending on the configuration for integrating the isenthalpic or isentropic expansion device with the separator and the form of separator employed, the isenthalpic or isentropic expansion step may be controlled so as to maintain LNG product specifications for stream 24 in FIGS. 1 through 5. Generally, the extent of the isenthalpic or isentropic expansion step can be controlled so as to reduce the non-combustibles content of the LNG by vaporizing more of these components and separating them into natural gas vapor component streams 13A and 13B for FIGS. 1 through 5. The isenthalpic or isentropic expansion step can also be controlled so as to maintain a particular ethane and higher boiling hydrocarbon mole percentage or to maintain a particular LNG product heating value as contemplated hereabove.

Additionally, the isenthalpic or isentropic expansion step may be controlled so as to permit the separation step to operate at an elevated pressure sufficient to convey natural gas vapor components to their desired end use system. Separation devices operating at near atmospheric pressure (such as those present in the prior art) and conveying vapor components to an end use system having a pressure of 300 psia require a compression ratio of over 20 to move these components to their end use system requiring substantial capital and operating resources. For this reason, the expanded pressure of the natural gas vapor component and the LNG component exiting the first expansion/separation step is generally in excess of about 75 psia, preferably in excess of about 125 psia, and more preferably in excess of about 175 psia for best results.

In another embodiment and as more fully detailed in FIG. 3, the cold natural gas vapor component 13A may be returned to the opposing side of heat exchanger 7 to provide additional refrigeration for natural gas stream 4. In a further enhancement of this embodiment and as more fully detailed in FIGS. 4 and 5, the additional refrigeration step and the separator may be integrated into a single device 12A. The cooled natural gas vapor component 13A, prior to leaving the separator 12A, may be utilized to further cool the natural gas stream 10 inside the separator itself. This cooling can be performed in a concurrent or countercurrent manner with the cooler natural gas vapor component 13A flowing in a heat transferring relationship to the opposing flow of the inlet natural gas stream 10. Heat transfer is preferably conducted in a countercurrent manner for best results. Suitable devices for performing such a function can include a fractionating or separating device comprising monolithic, plate, tubular or other heat transfer elements for transferring heat but not mass.

In embodiments, the present invention, as illustrated in FIGS. 1 through 5, incorporates at least two and preferably three isenthalpic or isentropic expansion combined with separation steps for best results. For example, FIGS. 1 through 3 depict a first isenthalpic or isentropic expansion device 9 for expanding cooled natural gas from conduit 8 and directing the expanded and further cooled natural gas to conduit 10. The further cooled natural gas 10 is thereafter separated into a cold natural gas vapor component 13A and a first LNG component 19 whereafter the first LNG component 19 is again expanded in an isenthalpic or isentropic expansion device 21. The twice-expanded LNG component is separated into a second cold natural gas vapor component 13B and a second LNG product stream 24. FIG. 3 additionally provides successive cooling steps 7 and 20 for utilizing first and second cold natural gas vapor components 13A and 13B for further cooling first LNG component 19 and second LNG product stream 24 respectively.

Figure 4:
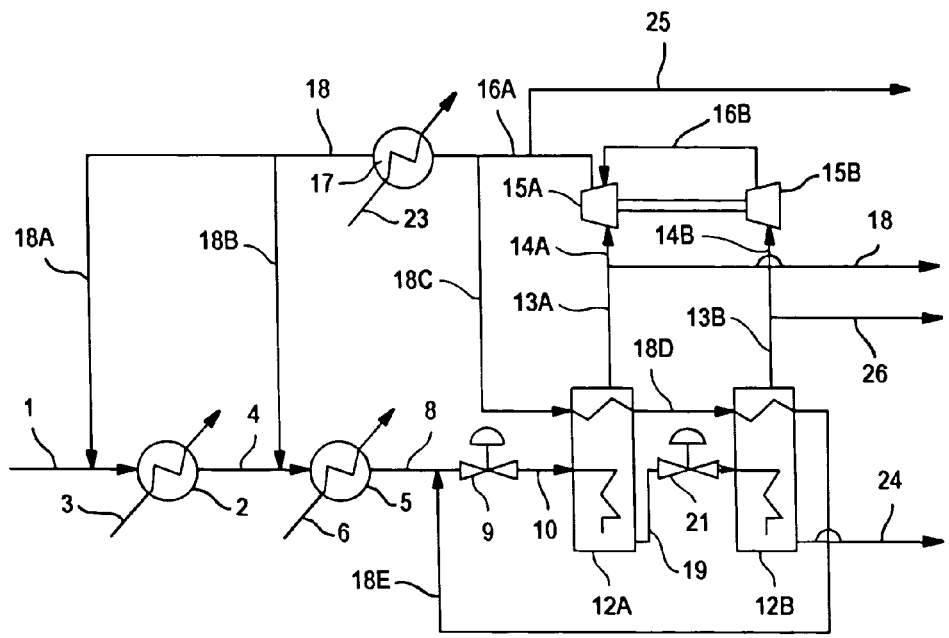
FIG. 4 is directed to an integrated process for producing LNG and GTL products which includes a first isenthalpic or isentropic expansion, followed by a separation step for producing a first LNG component, followed by a second isenthalpic or isentropic expansion and a second separation step wherein heat transfer between the separated natural gas vapor from each separation step and the natural gas directed to each respective isenthalpic or isentropic expansion step are each conducted in an integrated single separation/cooling device and wherein the separated natural gas from both separation/cooling steps is conveyed to an integrated compression step.
Figure 5:
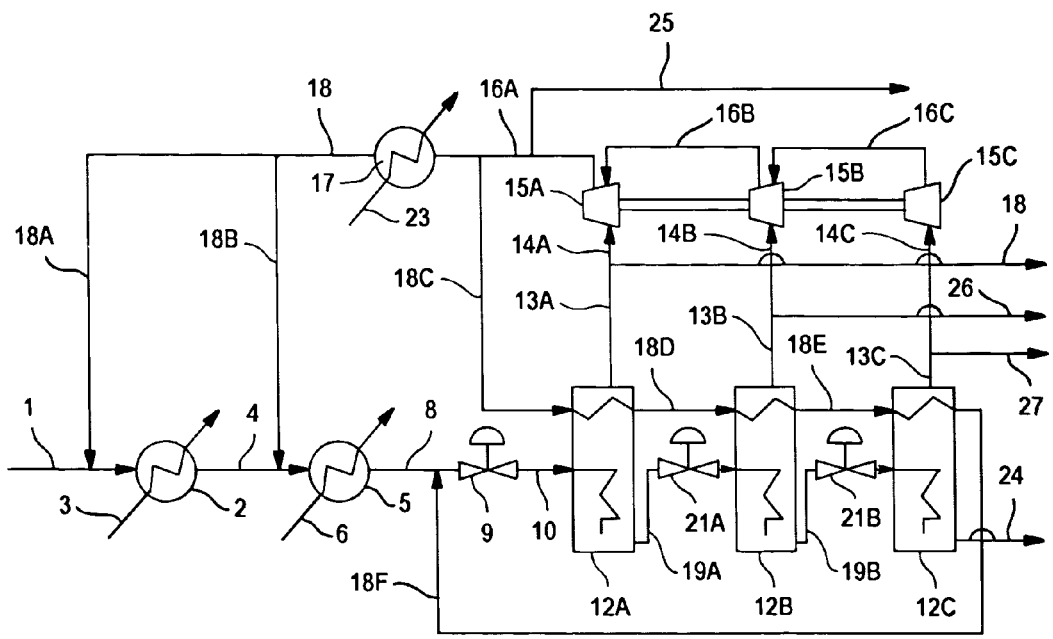
FIG. 5 is directed to an integrated process for producing LNG and GTL products which includes a first isenthalpic or isentropic expansion, followed by a separation step for producing a first LNG component, followed by a second and a third isenthalpic or isentropic expansion and a second and a third separation step wherein heat transfer between the separated natural gas vapor from each separation step and the LNG components directed to each respective isenthalpic or isentropic expansion step are each conducted in an integrated single separation/cooling device and wherein the separated natural gas vapor from all three separation/cooling steps is conveyed to an integrated compression step.

Embodiments of the present invention as illustrated in FIGS. 4 and 5 perform the multiple separation and secondary cooling steps in a single integrated device. For example, FIGS. 4 and 5 illustrate a first isenthalpic or isentropic expansion 9 followed by an integrated separation and cooling apparatus 12A for producing a cooled natural gas vapor component 13A and a first LNG component 19 or 19A. The first LNG component 19 or 19A is again expanded in a second isenthalpic or isentropic expansion device 21 or 21A and directed to a second integrated separation and cooling apparatus 12B for producing a second cooled natural gas vapor component 13B and a second cooled LNG component 24 (FIG. 4) and 19B (FIG. 5). For FIG. 5, the second cooled LNG component 19B is expanded a third time in a third isenthalpic or isentropic expansion 12C for producing a cooled natural gas vapor component 13C and a third cooled LNG product 24.

Multiple isenthalpic or isentropic expansion steps followed by subsequent separation steps provides substantial advantages over a single isenthalpic or isentropic expansion step followed by a single separation step.

Multiple separation steps, as contemplated in FIGS. 1 through 5 improve the separation of the cooled natural gas vapor component from the cooled LNG component and LNG product. For example, single expansion and separation steps, provided as a single stage flash provide only one theoretical stage of separation which may or may not provide adequate or desirable separation. More undesirably, however, single expansion and separation steps must be performed at atmospheric pressure and very low temperatures in order that an LNG product is produced from that separation step. Performing at least two expansion and separation steps permits a first step to be performed at a higher pressure thereby permitting a finer, more precise, or more flexible separation of non-combustibles and GTL Phase feed from the LNG component or LNG product. Furthermore, this higher pressure and more precise separation may be performed at a higher and more easily attainable temperature.

At least two and preferably three expansion and separation steps are further provided because the natural gas vapor component can be made available at more preferable supply pressures thus reducing overall energy requirements and equipment costs for integrating a LNG and GTL plant. Intermediate or end uses contemplated for the separated natural gas vapor component, to the extent that the stream or fractions thereof are available at differing compositions or process conditions, include cooling and recirculation back to LNG production (at one or several points along the LNG refrigeration train), purging to flare, or internal fuel uses such as for gas turbine fuel requirements, stream methane reformer fuel requirements, combined-cycle turbine fuel, or furnace fuel such as for heaters attendant to a hydrocracking facility for processing Fischer Tropsch GTL products.

Regarding the benefits of separated natural gas vapor component supply pressure flexibility, FIGS. 1 through 4 are directed to processes having two integrated isenthalpic or isentropic expansion and separation steps in series. In each first separation step, 11A or 12A as the case may be, a cooled natural gas vapor component 13A is provided at a higher pressure than the cooler natural gas vapor 13B available from the second separation. Each of these separated and cooled natural gas vapor components 13A and 13B, without compression, can be conveyed to consumption points based on composition specifics and pressure.

For example, the higher pressure separation device 11A or 12A of FIGS. 1 through 4 generally separates a cooled natural gas vapor component 13A containing a higher concentration of non-combustibles than the lower pressure separation devices 11B, 12B or 12C respectively would produce. This noncombustible-rich cooled natural gas vapor stream 13A is preferably directed to a fuel consumption point or to GTL feedstock rather than back to LNG production. As will be described later, incrementally directing noncombustible components to the integrated GTL facility is generally preferred to permitting those noncombustible components to remain in the LNG product.

In addition, the various fuel consumption points or feed locations for the integrated LNG and GTL facility of the present invention may preferably require higher or lower pressures as the case may be. For example, the high pressure separating device 11A or 12A of FIGS. 1 through 4 can synergistically provide a cooled natural gas vapor component 18 at sufficient pressure so as to offset GTL feed compression horsepower requirements or eliminate entirely the need for a separate GTL feed compressor. Lower pressure separation device 11B or 12B of FIGS. 1 through 4 can provide sufficient pressure to convey cooled natural gas vapor component 26 to consumption points such as furnace, refrigeration compressor or GTL fuel. Moreover, compression sources 15A and 15B provide the additional capability of supplying higher pressure compressed natural gas vapor components 16 and 25, to GTL feed or for cooling and recycle to LNG components or product. Operationally, cooled natural gas vapor components, available at any one of several pressures, provides flexibility for supplying optimum feed pressures to the GTL Phase.

FIG. 5 illustrates a process comprising three integrated isenthalpic or isentropic expansion and separation steps in series. The process embodied in FIG. 5 achieves most of the benefits set forth for two integrated step processes in addition to providing a third isenthalpic or isentropic expansion step and at least one additional theoretical stage of separation.

The processes set forth in FIGS. 2, 4, and 5 feature additional synergies by consolidating the compression steps performed by compressors or compressor stages 15A, 15B, and 15C into linked devices having common equipment and other related infrastructure and discharging to a common compressed gas system. For example, the processing steps embodied in devices 15A and 15B for FIGS. 2 and 4 and devices 15A, 15B, and 15C for FIG. 5 may be performed in varying stages of the same integrated device or at varying locations or positions along a single stage of the same device. In another embodiment, devices 15A and 15B for FIGS. 2 and 4 and devices 15A, 15B, and 15C for FIG. 5 may be integrated with isentropic expansion steps 9 and 21 for FIGS. 1 through 4 and steps 9, 21A and 21B for FIG. 5. In addition to the capital and operating cost advantages attendant to consolidating multiple compression stages into a single device, such an enhancement better ensures consistent and steady machine loading resulting in improved reliability.

The processes set forth in FIGS. 4 and 5 additionally illustrate capability for compressing cooled natural gas vapor components 13A, 13B, and 13C in compressors 15A, 15B, and 15C, cooling the compressed natural gas vapor component 16A in heat exchange device 17 and recirculating or recycling a portion of cooled natural gas vapor component 18 to the LNG train either prior to heat exchange step 2 through conduit 18A or prior to heat exchange step 5 through conduit 18B.

In another embodiment as illustrated in FIGS. 4 and 5, a portion of the compressed natural gas vapor component 18C may be directed to high pressure separating devices 12A, 12B, and/or 12C, as the case may be, so as to provide supplementally cooled streams 18D, 18E, and 18F for directing back to cooled natural gas stream 8 upstream of isenthalpic or isentropic expansion device 9.

In a preferred embodiment, the flow of stream 18 can be eliminated by directing the entire discharge from compressor 15A to stream 25. In this manner, throughput capacity of the LNG train otherwise consumed by either of streams 18A and 18B may be replaced by additional natural gas feed which will allow the processing of higher capacity through the LNG Phase without significantly changing the power consumption. Furthermore, an additional benefit may be derived from this embodiment since stream 25 would not likely require as high a pressure (depending on whether it is directed to the GTL Phase, fuel, or the like) as would be required to recycle this flow back to the LNG train through streams 18A and 18B. This benefit, realized through lower horsepower requirements from compressor 15A, would reduce the power requirements of the methane cycle, resulting in an increase in LNG product for a fixed plant power input.

The integrated process of the present invention as described in the embodiments of FIGS. 1 through 5 synergistically provides the capability of optimally managing heat transfer, compressor and other equipment energy requirements and product quality criteria for both LNG and GTL manufacture.

GTL Phase of Integrated Process

Suitable feedstock(s) from the LNG Phase of the integrated process for directing to the GTL Phase of the Integrated process may generally include stream 18 (FIGS. 1 through 5), stream 25 (FIGS. 1 through 5), stream 26 (FIGS. 1 through 5), stream 16 (FIG. 1), and stream 27 (FIG. 5). The preferred feedstock(s) for the integrated process of the present invention are streams 18, 25, and 26 with streams 18 and 26 being most preferred for best results. The suitable feedstock or preferred streams can be directed to various positions along the integrated GTL Phase of the process or can be combined and directed to the GTL Phase at a single position. For purposes of discussion and FIG. 6, GTL Phase feedstock 30 shall be construed to mean any one or all of stream 18 (FIGS. 1 through 5), stream 25 (FIGS. 1 through 5), stream 26 (FIGS. 1 through 5), stream 16 (FIG. 1), and/or stream 27 (FIG. 5).

The preferred GTL Phase feedstock can surprisingly comprise a higher mole percentage of non-combustible components and lower molecular weight hydrocarbon than is present in the natural gas feed to an LNG plant or than is common for traditional GTL feedstock. It has been found that incrementally directing these components from the LNG product to GTL feedstock can provide several benefits compared to the first generation of plants described in the prior art. Among these benefits include providing an improved, higher value LNG product having a lower mole percentage of non-combustibles than would generally be found in a non-integrated LNG plant.

In addition to the benefits associated with providing a higher quality product, the reduced presence of non-combustibles in the LNG product reduces the penalties associated with storing the LNG product with components lighter than methane and having to vent and recover or consume such non-combustibles from storage. Venting and consuming non-combustibles from storage inevitably consumes or destroys valuable LNG along with such non-combustibles. Furthermore, undesirable recycle of light, non-combustible components such as to stream 18 in FIGS. 4 and 5, will reduce the molecular weight of streams 10 and 19 for FIG. 4 and streams 10, 19A, and 19B for FIG. 5, therefore requiring lower refrigerating and operating temperatures and a higher energy load for liquefaction. These lighter streams also result in additional venting through streams 13A, 13B, and 13C for FIGS. 4 and 5, resulting in substantial internal recycle volume expansion and substantially higher production costs per unit volume of LNG produced.

Figure 6:
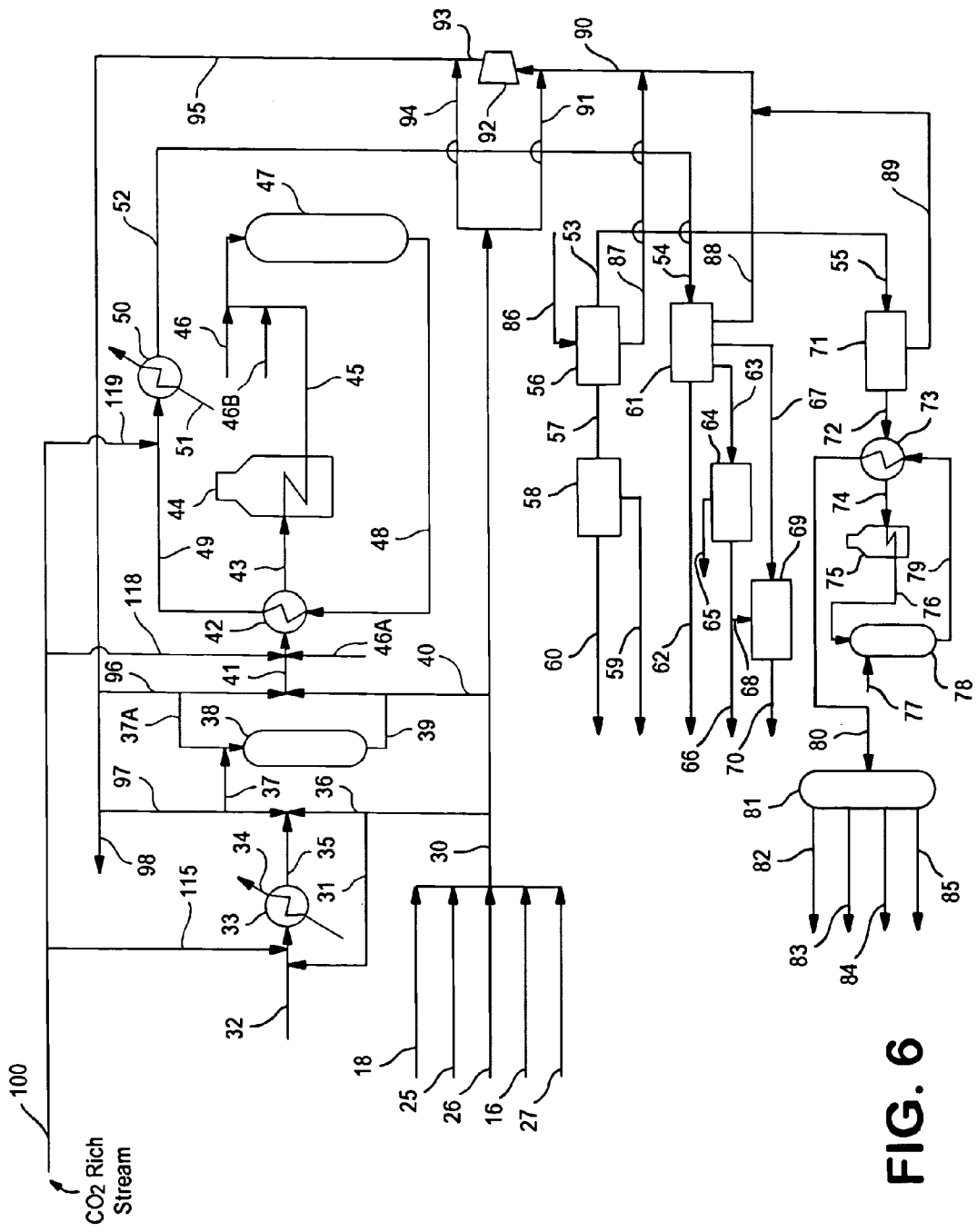
FIG. 6 is directed to a suitable GTL Phase for the integrated process for producing LNG and GTL products that utilizes an indirect synthesis gas route for producing methanol, dimethyl ether, dimethoxy methane, hydrogen, carbon dioxide, and/or Fischer Tropsch products.

FIG. 6 provides an example of a suitable GTL Phase for the integrated process of the present invention utilizing an indirect synthesis gas route for producing methanol, and optionally, one or more additional GTL products selected from dimethyl ether, dimethoxy methane, and/or Fischer Tropsch products. The GTL Phase in accordance with FIG. 6 illustrates that the invention can also be configured to produce hydrogen and carbon dioxide.

In FIG. 6, a portion of GTL Phase feedstock 31, supplemented if and as appropriate by pretreated natural gas 32 (which may include $CO_2$ therein), which is directed to preheat exchanger 33 for preheating the GTL feedstream to pre-reforming conditions. The heat source stream 34 for preheat exchanger 33 is generally provided from feed/effluent heat transfer with the hot effluent being made available from downstream processing steps. However, saturated or superheated steam can also be used for preheat.

The preheat exchanger outlet stream 35 can be supplemented by a portion of or an additional portion of GTL Phase feedstock 36 to form pre-reforming feedstock 37 before entering pre-reforming step 38. Pre-reforming step 38 is provided so as to improve the GTL feedstock quality by converting ethane and higher boiling point hydrocarbon by passing feedstock 37, in the presence of steam 37A, over a catalyst suitable for converting ethane and higher boiling point hydrocarbon into synthesis gas (and to a lesser extent methane). Suitable catalysts for the pre-reforming reaction generally include a high activity nickel containing-catalyst. Excessive amounts of higher boiling point hydrocarbon passing to the synthesis gas reforming or manufacturing section can result in the formation of coke contaminants thereby causing soot formation, catalyst bed or tube pluggage, and reduced catalyst activity.

Pre-reformer effluent stream 39 exits pre-reformer 38 where it may be supplemented by a portion of or an additional portion of GTL Phase feedstock 40 to form reformer feedstock 41. Reformer feedstock 41 is directed to preheat exchanger 42 for preheating the preheated reformer feedstock 43 so as to offset the heating requirements demanded of furnace 44. Furnace 44 is provided for preheating reformer feed 45 to synthesis gas reforming conditions. The heat source stream 48 for preheat exchanger 42 is generally provided through feed/effluent heat transfer from the products of the reforming reaction although saturated or superheated steam can also be used for preheat.

Furnace or fired heater 44 provides sufficient energy to the reformer feed 45 so as to maintain the optimal temperature conditions for the selected natural gas reforming step 47 technology. Suitable reforming technology and suitable natural gas reforming steps generally include steam methane reforming, as such reforming can produce a relatively high hydrogen to carbon oxide molar ratio which may be efficiently used to produce methanol.

Steam methane reforming generally contemplates reacting steam and natural gas at high temperatures and moderate pressures over a reduced nickel-containing catalyst so as to produce synthesis gas. Where synthesis gas reforming step 47 utilizes stream reforming technology, stream 46A comprises steam or water and stream 43 is heated in furnace 44 so as to provide a reforming reaction temperature, measured at the reactor outlet, generally in excess of 500° F., preferably ranging from about 1000° F. to about 2000° F., and more preferably from about 1500° F. to about 1900° F. for best results. The reaction pressure for steam reformer 47 is generally maintained at between 50 psig and 1000 psig, preferably at between 150 psig and 800 psig, and more preferably at between 250 psig and 600 psig for best results.

The effluent 48 from the synthesis gas reforming step 47 generally comprises hydrogen and carbon monoxide with generally lesser amounts of carbon dioxide, steam, methane and non-combustibles. The range of the molar ratio of hydrogen, carbon monoxide, and carbon dioxide is generally customized so as to most efficiently produce the downstream products of the particular GTL Phase. For Fischer Tropsch products, the hydrogen to carbon monoxide molar ratio will generally range from about 1.5 to about 2.5 and more preferably from about 2.0 to about 2.1 for best results. For methanol, dimethyl ether or dimethoxymethane production, the hydrogen minus carbon dioxide to carbon monoxide plus carbon dioxide molar ratio will generally range from about 1.5 to about 2.5 and more preferably from about 2.0 to about 2.1 for best results.

In FIG. 6, effluent 48 from the synthesis gas reforming step 47 is utilized in heat exchanger 42 for reformer preheat resulting in a cooler stream 49 which may still be too high in temperature for the particular downstream reaction step contemplated. Stream 49 is further cooled in heat exchanger 50 for providing a cooled synthesis gas stream 52 suitable for downstream conversion. Stream 49 can be cooled through feed/effluent heat exchange or can be utilized to produce or to superheat steam or to sensibly heat boiler feed water 51.

GTL products that are derived from the indirect synthesis gas route include, but are not limited to, methanol, dimethyl ether, dimethoxy methane, polydimethoxy methane, urea, ammonia, fertilizer and Fischer Tropsch reaction products. The Fischer Tropsch reaction produces products of varying carbon chain length, useful for producing lower boiling alkanes, naphtha, distillates useful as jet and diesel fuel and furnace oil, and lubricating oil and wax base stocks.

FIG. 6 illustrates the integrated process of the present invention with the option of producing any or all of carbon dioxide, hydrogen, methanol, dimethyl ether, dimethoxy methane, and Fischer Tropsch products including light hydrocarbon, naphtha, distillates useful as jet and diesel fuel and furnace oil, and lubricating oil and wax base stocks.

Synthesis gas stream 52 is shown in FIG. 6 as split into three streams for directing to independent or to potentially integrated downstream conversion systems comprising a first conversion system comprising hydrogen manufacture, a second conversion system comprising methanol, dimethyl ether, and dimethoxy methane manufacture, and a third conversion system comprising Fischer Tropsch product manufacture. However, it should be understood that not all three systems must be employed in the practice of the invention.

First effluent stream 53 and stream 86 comprising steam and/or water are directed to a water/gas shift reaction step 56 substantially shifting and raising the molar ratio of hydrogen to carbon monoxide in the synthesis gas. The hydrogen-enriched synthesis gas 57 is directed to a carbon dioxide removal step 58 for purifying the hydrogen. The hydrogen can be purified through any of several process routes known to those skilled in the art. Although the end use may define the hydrogen purity requirements and any selection of technology, suitable processes could include membrane separation, amine or hot potassium carbonate scrubbing systems, molecular sieves in pressure swing absorbers (PSA), or methanation reactors and the like, either singularly or in various combinations.

The hydrogen produced 59 from the carbon dioxide removal step 58 can be utilized internal to the GTL process for catalyst reactivation, for synthesis gas molar ratio control, for downstream product hydroprocessing/upgrading such as hydrotreating, hydrocracking, isomerization, or for fuel. The hydrogen stream 59 may also be exported for external uses including fuel cells, hydroprocessing, desulfurization or other external processes requiring relatively pure hydrogen. The carbon dioxide removed 60 through the carbon dioxide removal step 58 can also be utilized internally for synthesis gas molar ratio control, methanol production, carbon dioxide-methane reforming or can be used externally for uses such as enhanced oil recovery.

Second effluent stream 54 is directed to a methanol reaction step 61 for manufacturing methanol 62 which can be utilized for sale into the methanol market or internally or externally converted to other products such as olefins, acetic acid, formaldehyde, ethers such as but not limited to, methyl tertiary butyl ether (MTBE), ethyl tertiary butyl ether (ETBE), tertiary amyl methyl ether (TAME) and the like, and other chemical products produced from methanol.

Further integration of the LNG Phase with the GTL Phase is shown in FIG. 6, wherein according to the invention, a $CO_2$ rich stream 100 obtained by pretreatment of the natural gas feed to the LNG Phase as previously described herein (the pretreatment step is not shown) is also directed to the GTL Phase for use in production of methanol and other methanol derivatives. The $CO_2$ rich stream 100 can contain substantially pure $CO_2$, i.e., greater than 99.9 mole percent $CO_2$ based on total stream, as obtained from the pretreatment methods previously described, but may contain minor amounts, such as less than 5 mole percent, and preferably less than 1 mole percent, and more preferably less than 0.1 mole percent of other constituents, such as hydrocarbons and non-combustibles as contained in the natural gas stream employed. The $CO_2$ rich stream may be fed to the GTL Phase at a number of points, either upstream from the pre-reformer 38 or reformer 47, or downstream of the reformer 47. Preferably, the $CO_2$ rich stream is fed to the GTL Phase upstream of the reformer 47. In FIG. 6, the $CO_2$ rich stream is shown split into three separate streams: line 115 may be used to feed the $CO_2$ rich stream at a point upstream of pre-reformer 38, line 118 may be used to feed the $CO_2$ rich stream upstream of the reformer 47, and line 119 may be used to feed the $CO_2$ rich stream at a point downstream of the reformer 47. Any one or more of these lines may be used to feed the $CO_2$ rich stream to the GTL Phase. Other points for feeding the $CO_2$ rich stream to the GTL Phase are also contemplated, as will be evident to those skilled in the art upon reading the disclosure contained herein.

Methanol 63 from the methanol reaction step 61 can also be directed to a dehydrogenation step 64 for removing water 65 from methanol and producing dimethyl ether 66. Dimethyl ether 66 can be used as an aerosol or as a transportation, industrial or commercial fuel, can be source of hydrogen through a low temperature reforming step for both stationary and transportation fuel cells, and can be used as a source for olefins or gasoline via reactions over zeolitic catalysts.

Methanol 67 from the methanol reaction step 61 and dimethyl ether 68 from the dehydrogenation step may also be reacted in an oxidative condensation reaction step 69 involving the intermediate formation of formaldehyde to produce dimethoxy methane or polydimethoxy methane 70. Dimethoxy methane or polydimethoxy methane 70 can also be used as a transportation, industrial, or commercial fuel and show special promise as a fuel additive for conventional diesel fuel.

Third effluent stream 55 is directed to a Fischer Tropsch reaction step 71 for manufacturing Fischer Tropsch reaction products 72. Fischer Tropsch synthesis generally exothermically reacts hydrogen and carbon monoxide over either an iron or cobalt based catalyst to produce a range of hydrocarbon products. The specific hydrocarbon product distribution depends strongly on both the catalyst and the reactor temperature. Generally, the higher the reactor temperature, the shorter the average hydrocarbon product chain length. The Fischer Tropsch reaction can be conducted in any of several known reaction devices such as, but not limited to, a slurry reactor, an ebullated bed reactor, a fluidized bed reactor, a circulating fluidized bed reactor, and a multi-tubular fixed bed reactor.

In accordance with embodiments of the integrated process of the present invention, suitable Fischer Tropsch internal reactor temperature is generally in excess of 350° F., preferably ranges from about 350° F. to about 650° F., and more preferably from about 400° F. to about 500° F. for best results. The Fischer Tropsch reaction pressure is generally maintained at between 200 psig and 600 psig, preferably at between 250 psig and 500 psig, and more preferably at between 300 psig and 500 psig for best results.

Subsequent processing steps for Fischer Tropsch reaction products will depend on the products that the manufacturer desires to produce which in turn will depend on the geographical markets available to the manufacturer. However, Fischer Tropsch products 72 often contain a substantial portion of highly paraffinic straight-chained hydrocarbon comprising waxy components having a high pour point. These waxy products may not be easily transported through conventional transportation means such as pipelines. Hydrocracking or hydroprocessing Fischer Tropsch products can result in substantially improved flow properties so as to facilitate storage and transport of the products. Additionally, hydrocracking or hydroprocessing may also convert the highly paraffinic straight-chained hydrocarbon into products that can realize a higher market return.

In contemplation of hydrocracking or hydroprocessing, Fischer Tropsch reaction product 72 is directed to preheat exchanger 73 for preheating Fischer Tropsch reaction products 72 and directing the preheated Fischer Tropsch products 74 to furnace or fired heater 75. Furnace or fired heater 75 is generally operated at a transfer line 76 temperature sufficient to facilitate the hydrocracking reaction.

The hydrocracking or hydroprocessing reaction step 78 generally reacts a hydrocracking hydrocarbon feedstock 76 with hydrogen 77 in the presence of a catalyst comprising cobalt, nickel, molybdenum, tungsten, vanadium, palladium, platinum, or combinations thereof on an amorphous or molecular sieve support at reactions conditions suitable for converting such feedstock 76 into more marketable hydrdocracked products. Hydrocracking processing conditions generally comprise a reaction temperature ranging from about 500° F. to about 800° F., and more preferably from about 600° F. to about 750° F. for best results. Hydrocracking reaction pressure is generally maintained at between 500 psig and 5000 psig and preferably between 800 psig and 2000 psig for best results. Preferred reaction conditions will generally be a function of catalyst composition, hydrogen purity, product specifications, and other processing and equipment considerations and may be adjusted over the run length of the catalyst.

The product of the hydrocracking or hydroprocessing reaction 79 is generally directed back to preheat exchanger 73 so as to reduce the heating load required of furnace or fired heater 75. The hydrocracked product 80 is thereafter fractionated in fractionator or distillation tower 81 for conversion into marketable products.

The marketable products from fractionator 81 include low boiling point light hydrocarbon gases 82 such as methane, ethane, propane and butane which can be directed to fuel uses, back to the LNG Phase for recovery, to pre-reforming step 38 or reforming step 47, or for further separation and marketed as commodity products, gasoline boiling range naphtha 83 useful for further upgrading to gasoline or other chemical grade products such as olefins and aromatics, distillate boiling range products 84 such as jet and diesel fuel and furnace oil, and higher boiling point lubricating oil base stock 85. The products produced through a Fischer Tropsch reaction can be highly paraffinic and generally contain very low levels of sulfur making these products quite environmentally favorable.

The independent or potentially integrated downstream conversion steps comprising the first conversion system comprising hydrogen manufacture 56, the second conversion system comprising methanol, dimethyl ether, and/or dimethoxy methane manufacture 61, and the third conversion system comprising Fischer Tropsch product manufacture 71 may not and generally do not fully convert all of the synthesis gas provided through conduits 53, 54, and 55 respectively into products. Unconverted synthesis gas 87 from the first conversion system 56, unconverted synthesis gas 88 from the second conversion system 61, and unconverted synthesis gas 89 from the third conversion system 71 can be individually recycled to such conversion systems for conversion to products or can be returned to the synthesis gas manufacturing step for reformation into synthesis gas at more optimal composition and conditions.

In FIG. 6, unconverted synthesis gas conduits 87, 88, and 89 are combined so as to form conduit 90 for directing unconverted synthesis gas to synthesis gas recycle compressor 92. Prior to entering the suction side of recycle compressor 92, the unconverted synthesis gas can be supplemented with a portion of GTL Phase feedstock 91. The substantial benefit to providing GTL Phase feedstock through conduit 91 in accordance with this embodiment of the present invention is the possibility for eliminating the need for a GTL feed compressor thereby reducing capital cost and eliminating the need to operate and maintain separate devices.

Synthesis gas compression step 92 is provided for compressing streams 90 and 91 to a higher pressure and producing a compressed synthesis gas feed/recycle stream 93. Suitable compression devices can include a gas or steam driven turbine or motor driven device for isentropically compressing a gas to a higher pressure. Depending on the distinct source pressures of streams 91 and 90, the compression step 92 may be further enhanced by performing the compression step at varying stages of an integrated multi-stage device or at varying locations or positions along a single stage of the same device. In addition to the capital and operating cost advantages attendant to consolidating multiple compression stages into a single device, such an enhancement better ensures consistent and steady machine loading resulting in improved reliability. Depending on the composite composition of streams 90 and 91, another benefit of the compression step 92 may be an increase in temperature thereby reducing energy consumption otherwise required to reprocess these streams.

In another embodiment of the present invention, compressed unconverted synthesis gas 93 can be supplemented with a portion of GTL Phase feedstock 94. Where GTL Phase feedstock 94 is available at a pressure in excess of that required for recompression to the synthesis gas conversion section, it is preferred to add this GTL Phase feedstock to the unconverted synthesis gas after compression step 92 so as to avoid recompression cost. The compressed unconverted synthesis gas and GTL Phase feedstock 93 supplemented by any additional GTL Phase feedstock 94 can be combined into conduit 95 for return to the synthesis gas conversion system.

Suitable locations for feeding or returning any composite streams of unconverted synthesis gas and GTL Phase feedstock to the GTL Phase include injecting stream 97 into pre-reformer feed 37 or reformer feed 41. Where the composite stream of unconverted synthesis gas and GTL Phase feedstock comprises a substantial amount of ethane and higher boiling point hydrocarbon, it is preferred that the composite stream be injected into stream 37 for best results. Where the composite stream of unconverted synthesis gas and GTL Phase feedstock is reliably lean in ethane and higher boiling point hydrocarbon, the composite stream may be injected into stream 41. Where there is uncertainty of operation, it is preferred that unconverted synthesis gas and GTL Phase feedstock injection be made into stream 37 for lowest risk and best results.

An alternative routing for a portion of the unconverted synthesis gas and GTL Phase feedstock is to GTL Phase or LNG Phase fuel through conduit 98. In this manner, certain non-combustibles can be directed to fuel and purged from the integrated process. Fuel purging may also take place at the individual synthesis conversion systems so as to produce a recycle of unconverted synthesis gas comprising less non-combustibles.

As noted above, the preferred GTL Phase feedstock surprisingly comprises a higher mole percentage of non-combustible components than is present in the LNG product or than is common with traditional GTL feedstock. In addition to the benefits attendant to removing non-combustible components from the LNG product, the GTL Phase in accordance with the present invention is uniquely equipped to process incremental non-combustibles transferred from the LNG Phase to the GTL Phase.

The GTL Phase is generally designed and operated so as to facilitate the processing of any nitrogen, argon, or other constituents of air that may break through or across connecting oxygen-separation plants that are present with autothermal or catalytic partial oxidation reforming systems. The catalysts and reactor systems are designed to tolerate the presence of non-combustibles and purge systems exist so as to efficiently maximize energy recovery from any hydrocarbon that escapes along with any purge of non-combustibles. In addition, carbon dioxide or carbon monoxide that might otherwise cause operating penalties or risks in the LNG Phase were these components to remain in the system (i.e., through freeze risks, etc.), pose little risk or penalty in the GTL Phase where temperatures are elevated and carbon monoxide and carbon dioxide are basic products of the various reaction steps.

Overall, the integrated process of the present invention for producing LNG and GTL products provides substantial and synergistic benefits compared to non-integrated, standalone LNG and GTL plants, LNG and GTL plants sharing complementary infrastructure, and integrated NGL and LNG plants that only modestly integrate LNG and GTL manufacture.

The present invention in embodiments provides an integrated process for producing LNG and GTL products that incrementally shifts non-combustibles such as nitrogen and helium from the LNG Phase and LNG product to the GTL Phase and GTL feed where it can be cost effectively processed. The GTL Phase in accordance with the present invention can process non-combustibles utilizing existing systems while substantially recovering most of the energy content of any hydrocarbon that accompanies final processing of the non-combustibles. Non-combustibles otherwise remaining in the LNG Phase and LNG product often remain in the LNG product diminishing the quality and heating value of the product. As those non-combustibles remain in LNG product storage over time, these components often must be vented and can occasionally be lost to flaring.

The present invention in embodiments provides an integrated process for producing LNG and GTL products which synergistically permits a substantial portion of cooled natural gas vapor component or LNG component to be isentropically or isenthalpically expanded and directed to the GTL Phase for conversion to GTL products foregoing the need to recompress and refrigerate such material for reinjection back into the LNG refrigeration system or to reject such stream to fuel. At the same time such cooled natural gas vapor component or LNG component is being isentropically or isenthalpically expanded for directing to GTL conversion, the isentropic or isenthalpic expansion autorefrigerates and cools the separated and remaining LNG thereby providing a synergistic LNG refrigeration effect reducing the need for supplementary or external refrigeration. Moreover, where such cooled natural gas vapor component is recompressed for directing to such GTL Phase, the temperature of such cooled natural gas vapor component is increased thereby synergistically reducing preheating requirements in the GTL Phase.

The present invention in embodiments provides an integrated process for producing LNG and GTL products that facilitates the production of a LNG product containing a higher total mole percentage of ethane and higher boiling point hydrocarbon and therefore a higher energy content. In the alternative, the process of the present invention in embodiments can facilitate the production of a LNG product containing a higher energy content by reducing the mole percentage of light non-combustibles, beyond that which can be achieved with a single expansion and separation step performed at atmospheric pressure. LNG product having a higher energy content can be of great value in certain geographical markets. The process of the present invention features an isentropic or isenthalpic expansion of cooled natural gas followed by a separation step which can be easily and cost effectively operated so as to fractionate ethane and higher boiling point hydrocarbon into the LNG product. As another synergistic benefit to the foregoing, removing ethane and higher boiling point hydrocarbon from the GTL Phase feedstock and incrementally directing this material to LNG product is beneficial in that a GTL feedstock having lower concentrations of ethane and higher boiling point hydrocarbon reduces pre-reforming and reforming catalyst deactivation and improves overall GTL Phase operational reliability. As an additional flexibility, where the LNG Phase of the process of the present invention features multiple pressure stages of separation, the degree of incremental separation of ethane and higher boiling point hydrocarbon between the GTL Phase feedstock and the LNG product can be optimized so as to meet market and plant demands.

The process of the present invention in embodiments provides an integrated process for producing LNG and GTL products that synergistically and more efficiently utilizes available natural gas pressure while at the same time minimizing compressor capital requirements. For example, where GTL Phase feedstock can be supplied from either of one or more separators within the LNG Phase separation step, without further compression, the need for a distinct GTL feedstock compressor can be eliminated. Where the GTL Phase feedstock can be directed to an unconverted synthesis gas recycle gas compression step for recycling to the GTL Phase, the need for a distinct GTL feedstock compressor can be eliminated. Lastly, if the pressure of the GTL Phase feedstock after the isentropic or isenthalpic expansion remains higher than optimal, the expansion level can be increased resulting in recovery of this pressure energy and resulting in increased LNG Phase throughput for a fixed level or refrigeration horsepower.

The process of the present invention in embodiments provides an integrated process for producing LNG and GTL products that realizes a synergistic benefit from LNG Phase water removal in the integrated manufacture of GTL products. Substantially reducing the water content of the natural gas prior to the isenthalpic or isentropic expansion step results in a GTL feed stream comprising substantially less water. The lower water concentration of the natural gas feeding the GTL processing steps results in a substantial improvement in control of the synthesis gas hydrogen to carbon monoxide molar ratio which is operationally beneficial in converting synthesis gas into salable products.

Figure 7:
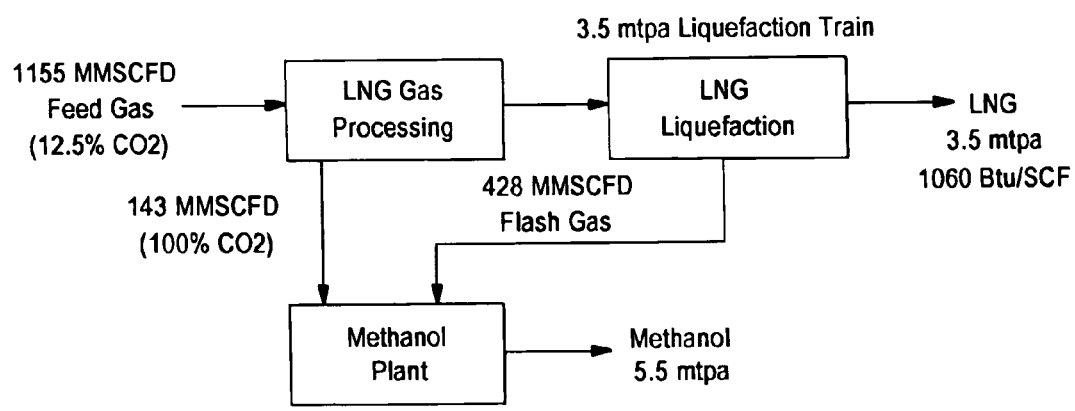
FIG. 7 is a simplified process flow diagram illustrating an integrated LNG and GTL process wherein a natural gas feed to an LNG phase is pre-treated to separate $CO_2$ therein as an essentially pure $CO_2$ stream prior to production of LNG products, and the resulting $CO_2$ is then directed to a GTL phase (comprising for example a methanol plant) wherein the $CO_2$ is employed to produce GTL products which include methanol. The flash gas obtained during liquefaction of the natural gas in the LNG phase is also directed to the GTL phase wherein the flash gas is employed to make synthesis gas by steam methane reformation. The resulting synthesis gas is reacted with the $CO_2$ to produce the methanol product.

FIG. 7 shows a simplified process flow diagram illustrating an embodiment of an integrated LNG Phase and GTL Phase wherein the $CO_2$ in a natural gas feed to the LNG Phase is utilized in production of methanol in the associated GTL Phase, as well as utilizing the flash gas from the LNG Phase to produce GTL Products, such as methanol, in the GTL Phase.

Figure 8:
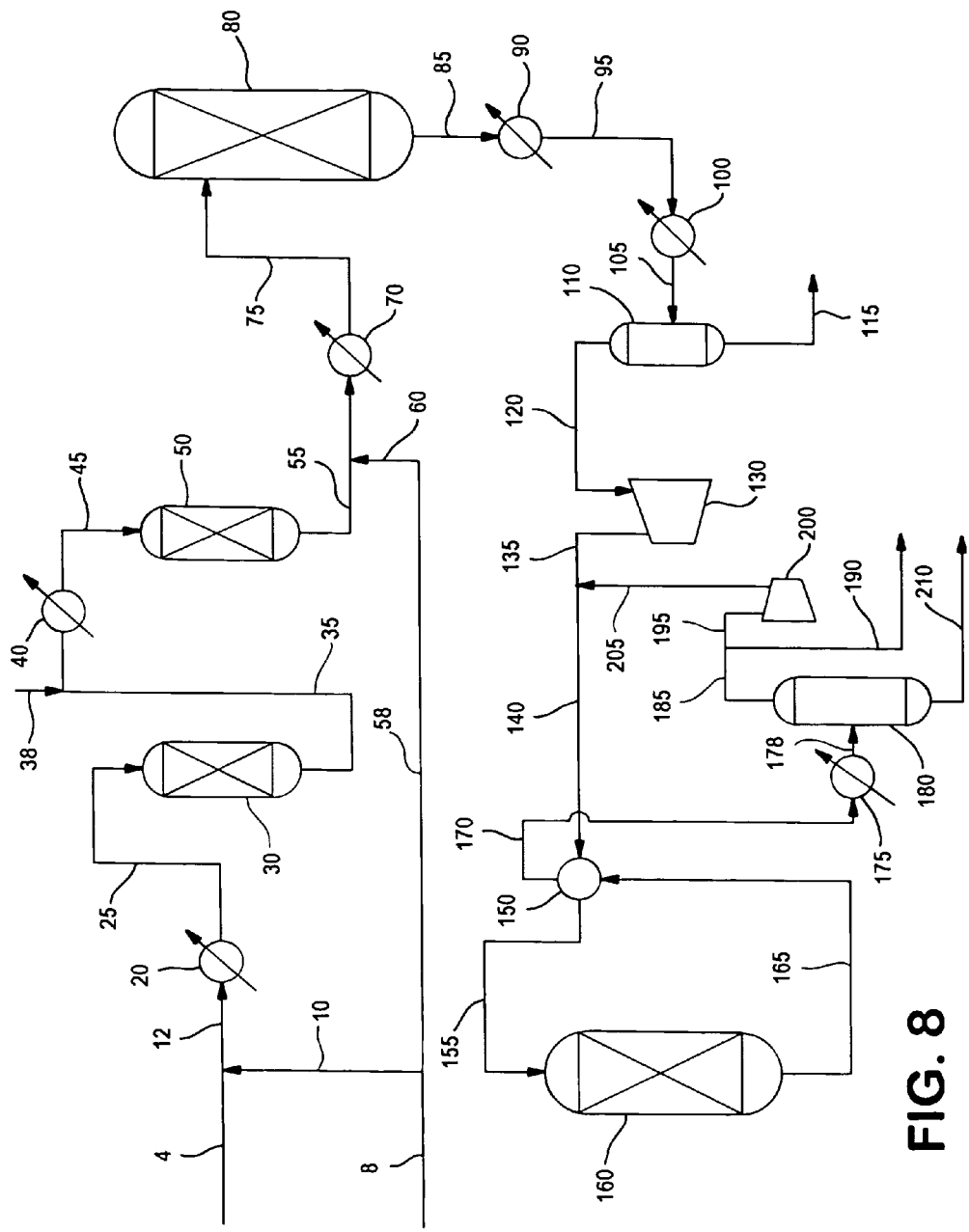
FIG. 8 is another process flow diagram illustrating a GTL Phase directed specifically to methanol production in accordance with the present invention.

FIG. 8 shows a process flow diagram illustrating a GTL Phase directed specifically to methanol production in accordance with the present invention, which comprises conversion of natural gas to synthesis gas ($H_2$ and CO) and then conversion of the synthesis gas to methanol. In the process, the non-combustible $CO_2$ gas separated from the raw natural gas prior to being fed to the LNG process is recovered and subsequently utilized in the production of methanol. The $CO_2$ can be converted to methanol by any known synthesis method, such as those illustrated for example in Vol. 16, pages 537–556 of the Kirk-Othmer Encyclopedia Of Chemical Technology (4$^{th}$ Ed.—John Wiley & Sons Inc. New York, N.Y. 1995), the teachings of which are incorporated herein by reference. The $CO_2$ can generally be readily reacted with hydrogen gas using any conventional methanol synthesis catalyst, such as a zinc-chromium oxide catalyst or copper-zinc-alumina catalyst as known in the art, to form methanol according to the following equation:

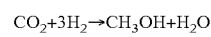

$$CO_2 + 3H_2 \rightarrow CH_3OH + H_2O$$

Hydrogen gas for the conversion may be obtained by taking a portion of the natural gas (either before or after pretreatment to remove $CO_2$ and other acid gases, such as $H_2S$) and reforming it, such as by steam methane reforming, to produce a synthesis gas with a $H_2$ to carbon oxide ratio favorable for efficient conversion to methanol. Generally, this stoichiometric molar ratio is expressed as follows:

$$S_n = [H_2 - CO_2]/[CO + CO_2]$$

which is generally from 1.5 to 2.5 and more particularly 2.0 to 2.1. As a result, $CO_2$ which would otherwise have been vented to atmosphere can be advantageously converted to higher value products, such as methanol and dimethyl ether.

In FIG. 8, separation of the $CO_2$ from the natural gas as produced from a reservoir is not shown for convenience, but may be done by any of a number of methods known to the art as mentioned herein.

As shown in FIG. 8, all or a portion of the $CO_2$ recovered from such pre-treatment steps may be conveyed by lines 8 and 10 and then combined with a natural gas stream in line 4 to produce a blended feed stream which is conveyed by line 12 to a heater 20. After being heated in heater 20, the blended feed stream is then conveyed by line 25 to a guard bed vessel 30 wherein any residual amount of sulfur-containing contaminants present in the blended feed stream may be removed by contact with an adsorbent bed, typically of zinc oxide. Alternatively, the $CO_2$ stream conveyed by lines 8 and 10 and natural gas stream conveyed by line 4 could be treated individually in such guard beds.

After treatment in the guard bed 30, steam is added to the blended feed stream via line 38. The blended feed stream is then conveyed by line 35 to heater 40 wherein the temperature thereof is further adjusted to from 300° C. to 450° C. prior to introducing the blended feed stream via line 45 to pre-reformer reactor vessel 50. Pre-reformer reactor vessel 50 typically contains a nickel-based reforming catalyst, but may be any of a number of reforming catalysts as known in the art, and is designed to convert higher hydrocarbons which may be present in the blended feed stream and produce a predominately methane-containing feed stream. Effluent from pre-reformer reactor vessel 50 is conveyed by line 55 to a heater 70 which heats the effluent to a temperature suitable for steam reforming of the methane-containing stream into synthesis gas, typically a temperature of from 400° C. to 500° C. In the event that the $CO_2$ feed in line 8 is substantially free of sulfur-containing compounds, such as less than 1 ppm, it is possible to add $CO_2$ to the process at the location identified as 60 on FIG. 8, by conveying all or part of the $CO_2$ to this location via line 58.

After being heated to a temperature suitable for steam reformation, the methane-containing stream is conveyed by line 75 to steam reformer vessel 80. Steam reformer vessel 80 typically contains a nickel-containing steam reforming catalyst, but may be any of those known in the art, which converts the methane-containing stream into one rich in synthesis gas, i.e., hydrogen gas and carbon oxides. The synthesis gas stream exiting steam reformer vessel 80 is conveyed by line 85 to a heat exchanger 90 where excess heat therein is recovered for other uses, such as in heaters 20 and 40. The synthesis gas stream is then conveyed by line 95 to a cooler 100 wherein the temperature is further reduced. The so-cooled synthesis gas stream is conveyed by line 105 to separator 110 wherein condensed water may be removed from the process by line 115. The synthesis gas stream is thereafter conveyed by line 120 to synthesis gas compressor 130 which compresses the stream to a pressure suitable for methanol production, such as 35 to 150 bar. The compressed synthesis gas stream is then conveyed by lines 135 and 140 to heat exchanger 150 wherein the temperature is adjusted to that suitable for methanol production, such as from 200° C. to 300° C.

After adjustment of temperature, the synthesis gas stream is conveyed by line 155 to methanol synthesis reactor 160. Methanol synthesis reactor 160 generally utilizes a catalyst, such as a copper-zinc-alumina catalyst as mentioned above, but may be any of those known in the art. Effluent from the methanol synthesis reactor 160 comprised mostly of methanol, water, and unreacted synthesis gas, is conveyed by line 165 to heat exchanger 150 wherein excess heat is recovered therefrom, and thereafter the effluent is conveyed by line 170 to cooler 175. Thereafter, the effluent is conveyed by line 178 to separator 180 wherein a crude methanol product is recovered through line 210 and a gaseous stream exits by line 185. A purge gas stream, which may be used as fuel gas, is taken off via line 190 and the remainder of the gaseous stream comprised of unreacted synthesis gas is directed by line 195 to recycle compressor 200 which recompresses the gaseous stream to that suitable for methanol synthesis as previously described. The compressed gaseous stream is directed by line 205 to line 135 and mixed with fresh synthesis gas.

The resulting methanol product from line 210 can then be purified by methods as known in the art, such as distillation, and then readily converted to DME as summarized on pages 538–539 of the Kirk-Othmer passage previously incorporated herein. In general, DME is prepared by dehydrating methanol over an acidic catalyst to produce dimethyl ether and water.

The present invention is described in further detail in connection with the following examples, it being understood that the same is for purposes of illustration and not limitation.

EXAMPLE 1

The process, substantially in accordance with the present invention and following the configuration set forth in FIG. 5, was compared against a process configuration wherein a LNG plant and a GTL plant operate separately. The comparisons were made using computer simulations with each configuration producing precisely the same volume of Fischer Tropsch GTL products and the same tonnage per day of LNG product so as to illustrate the substantial benefits provided through the integrated process of the present invention. The results of the comparison are set forth in Table 1.

TABLE 1

| Properties/Rates | Separate LNG/GTL Plants | | Integrated Process GTL From | |
|---|---|---|---|---|
| | LNG | GTL | LNG | LNG |
| Rate (MMSCFD) | 669 | 528 | 1198 | 545 |
| Feed | | | | |
| Composition (Mole %) | | | | |
| Nitrogen | 0.86 | 0.86 | 0.86 | 1.58 |
| Helium | 0.03 | 0.03 | 0.03 | 0.04 |
| Carbon Dioxide | 0.01 | 0.01 | 0.01 | 0.01 |
| Methane | 96.52 | 96.52 | 96.52 | 98.29 |
| Ethane | 2.00 | 2.00 | 2.00 | 0.08 |
| Propane | 0.43 | 0.43 | 0.43 | 0.00 |
| Butane | 0.15 | 0.15 | 0.15 | 0.00 |
| Pentane | 0.00 | 0.00 | 0.00 | 0.00 |
| Hexane | 0.00 | 0.00 | 0.00 | 0.00 |
| Total | 100.00 | 100.00 | 100.00 | 100.00 |

TABLE 1-continued

| Properties/Rates | Separate LNG/GTL Plants | | Integrated Process | |
|---|---|---|---|---|
| | LNG | GTL | LNG | GTL From LNG |
| Rate (MMSCFD) | 669 | 528 | 1198 | 545 |
| Products | | | | |
| Rate (Volume) | | | | |
| LNG (MMSCFD) | 588.7 | | 573.8 | |
| Naphtha (BPD) | | 16.299 | | 16.299 |
| Diesel (BPD) | | 41.980 | | 41.980 |
| Rate (Weight) | | | | |
| LNG (tonne/day) | 11.664 | | 11.664 | |
| Naphtha (tonne/day) | | 1.825 | | 1.825 |
| Diesel (tonne/day) | | 5.191 | | 5.191 |
| LNG Composition(Mole %) | | | | |
| Nitrogen | 0.06 | | 0.01 | |
| Helium | 0.00 | | 0.00 | |
| Carbon Dioxide | 0.01 | | 0.01 | |
| Methane | 97.01 | | 94.69 | |
| Ethane | 2.26 | | 4.08 | |
| Propane | 0.49 | | 0.90 | |
| Butane | 0.17 | | 0.31 | |
| Pentane | 0.00 | | 0.00 | |
| Hexane | 0.00 | | 0.00 | |
| Total | 100.00 | | 100.00 | |
| LNG Properties | 1042 | | 1066 | |
| Heating Value (Btu/SCF) | | | | |
| Process Power Consumption (KW/LNG tonne/day) | 14.9 | | 12.6 | |

Separate LNG/GTL Case

A natural gas feedstock having the composition set forth in Table 1 is fed separately to a LNG facility for producing LNG product and a facility for producing Fischer Tropsch products. The natural gas feedstock for the LNG facility was provided in an amount equal to 669 MMSCFD while the feedstock provided to the GTL facility was provided in the amount of 528 MMSCFD for a total of 1197 MMSCFD provided to both facilities. For this configuration, 11,664 tonnes/day of LNG and 7,016 tonnes/day of GTL products are produced of which 1,825 tonnes per day of the GTL product is naphtha and 5,191 tonnes per day is diesel fuel. The LNG product has a heating value of 1042 Btu/scf and the overall power consumption for both facilities is 14.9 kilowatts per LNG tonne per day.

Integrated Case

A natural gas feedstock having the composition set forth in Table 1 is fed to an integrated LNG/GTL process in accordance with the present invention substantially as illustrated in FIG. 5.

Referring to FIG. 5 as a reference diagram for this configuration, 1198 MMSCFD of natural gas is provided as stream 1 at a pressure of 830 psia and a temperature of 106° F. A portion of stream 1, in the amount of 600 MMSCFD, was split from stream 1 and directed to stream 18C for directing to high pressure separating devices 12A, 12B, and 12C, leaving 600 MMSCFD of natural gas feed for directing to cooling steps 2 and 6.

The split portion of stream 1 is directed to high pressure separating device 12A and high pressure separating device 12B in series where the natural gas is cooled prior to being isenthalpically expanded in an expansion step present along conduit 18E wherein the pressure is reduced to 645 psia and the temperature reduced to −57° F. A split portion of isenthalpically expanded stream 18E, in an amount equal to 240 MMSCFD, is recycled back to the natural gas stream after cooling step 2 at conduit 4. The remaining portion of isenthalpically expanded stream 18E, in an amount equal to 360 MMSCFD, is directed to high pressure separating device 12C where it is further cooled to −110° F. at a reduction in pressure to 640 psia and thereafter recycled to the natural gas stream after cooling step 5 at conduit 8.

The recombined and cooled natural gas stream 8 is isenthalpically expanded across a Joule Thompson valve 9 to provide a cool natural gas stream 10 at 645 psia and a temperature of −121° F. The cool natural gas stream 10 from the isenthalpic expansion step is directed to high pressure separating device 12A where it is separated through a single theoretical stage of separation into 369 MMSCFD of a first cooled natural gas vapor component 13A and 831 MMSCFD of a first cooled LNG component 19A, both provided at a pressure of 210 psia and a temperature of 60° F.

The first cooled LNG component 19A is isenthalpically expanded across a second Joule Thompson valve 21A and directed to second high pressure separating device 12B where it is separated through a single theoretical stage of separation into 132 MMSCFD of a twice cooled natural gas vapor component 13B and 699 MMSCFD of a twice cooled LNG component 19B, both provided at a pressure of 70 psia and −174° F.

The twice cooled LNG component 19B is isenthalpically expanded across a third Joule Thompson valve 21B and directed to a third high pressure separating device 12C where it is separated through a single theoretical stage of separation into 124 MMSCFD of a thrice cooled natural gas vapor component 13C and 575 MMSCFD of a final LNG product 19C, both provided at a pressure of 14 psia and −257° F.

The final LNG product 19C of the integrated process of the present invention desirably contains substantially less nitrogen than the comparison separate LNG/GTL process described hereabove (0.01 mole percent as compared to 0.06 mole percent). In addition, the LNG product of the integrated process of the present invention also has a higher heating value than the comparison separate LNG/GTL process (1066 Btu/scf as compared to 1042 Btu/scf). The higher heating value is attributed to a lower concentration of non-combustibles such as nitrogen and higher concentrations of ethane, propane and butane respectively. Both of these characteristics render the LNG product produced in accordance with the present invention beneficial for many commercial uses.

A portion of the first cooled natural gas vapor component 13A in an amount equal to 80 MMSCFD is removed from the cooled natural gas vapor component through conduit 18 and is utilized for internal fuel usage requirements. The balance of the first cooled natural gas vapor component 13A (provided at a pressure of 210 psia), twice cooled natural gas vapor component 13B (provided at a pressure of 70 psia), and thrice cooled natural gas vapor component 13C (provided at 14 psia) are directed to compression stages 15A, 15B, and 15C respectively of an integrated compression step for directing and conveying the combined natural gas vapor components 25 to the GTL Phase for conversion to GTL products.

The GTL Phase feedstock 25 is provided for GTL conversion in an amount equal to 545 MMSCFD and at a pressure of 400 psia and a temperature of 195° F. In a conventional LNG process, this compressed vapor stream, heated through the compression step, would often have to be inefficiently cooled, subcooled, and reinjected back into the LNG process for production of LNG. As is apparent from this example, not only can this subcooling step be eliminated but the heat of compression provided from compression stages 15A, 15B, and 15C can be gainfully employed in the GTL Phase of the process.

The composition of the GTL Phase feedstock 25 is set forth in Table 1. As is apparent from Table 1, the GTL Phase feedstock of the present invention retains substantially more of the non-combustible components such as nitrogen and helium. This results in an overall benefit for the integrated process of the present invention as GTL processes are generally better equipped to remove these materials at lower cost. More beneficially, the GTL Phase feedstock contains substantially less ethane and heavier hydrocarbon than the separate LNG/GTL process configuration. The presence of heavier hydrocarbon in a GTL facility generally requires costly separation equipment or prereforming steps to remove or converted these components to methane or syngas prior to the syngas reforming step so as not to deactivate the reforming catalyst.

The integrated process of the present invention also produces 11,664 tonnes/day of LNG and 7,016 tonnes/day of GTL products of which 1,825 tonnes per day of the GTL product is naphtha and 5,191 tonnes per day is diesel fuel. As noted above, however, the LNG product produced in accordance with the present invention has an enhanced heating value of 1066 Btu/scf as compared to 1042 Btu/scf for the separate LNG/GTL Case. In addition, the power requirements for achieving substantially the same production requirements is reduced to 12.6 kilowatts per LNG tonne per day from 14.9 kilowatts per LNG tonne per day for the separate LNG/GTL Case. This amounts to an energy reduction in excess of 15%.

Other embodiments and benefits of the invention will be apparent to those skilled in the art from a consideration of this specification or from practice of the invention disclosed herein. It is intended that this specification be considered as exemplary only with the true scope and spirit of the invention being indicated by the following claims.

We claim:

1. An integrated process for producing LNG products in a LNG Phase production zone and conversion of natural gas into GTL products that include methanol in a GTL Phase production zone from a natural gas comprising hydrocarbons and $CO_2$, the process comprising the steps of:
pre-treating at least a first portion of the natural gas to separate at least a portion of the $CO_2$ therefrom and produce a natural gas feed having reduced $CO_2$ content and a stream rich in $CO_2$;
converting the natural gas feed into an LNG product in the LNG Phase;
converting a second portion of the natural gas to a synthesis gas by steam methane reformation; and
reacting the stream rich in $CO_2$ with at least a portion of the synthesis gas in the GTL Phase to produce methanol.

2. The integrated process of claim 1 further comprising feeding the stream rich in $CO_2$ with the second portion of the natural gas such that the stream rich in $CO_2$ is mixed therewith prior to formation of the synthesis gas.

3. The integrated process of claim 1 wherein the natural gas has a methane content of at least 75 mole percent.

4. The integrated process of claim 1 wherein after pre-treatment, the natural gas feed having reduced $CO_2$ content has a $CO_2$ content of less than 0.01 mole percent based on the total feed.

5. The integrated process of claim 1 wherein the synthesis gas has a stoichiometric molar ratio of hydrogen, carbon monoxide, and carbon dioxide expressed as $S_n=[H_2-CO_2]/[CO+CO_2]$ of from about 1.5 to about 2.5.

6. The integrated process of claim 1 wherein the synthesis gas has a stoichiometric molar ratio of hydrogen, carbon monoxide, and carbon dioxide expressed as $S_n=[H_2-CO_2]/[CO+CO_2]$ of from about 2.0 to about 2.1.

7. The integrated process of claim 1 wherein the steam methane reforming is conducted by reacting steam and the natural gas over a reduced nickel-containing catalyst at a temperature in excess of 500° F. and a pressure of from between 50 psig and 1000 psig.

8. The integrated process of claim 7 wherein the temperature is from 1500° F. to 1900° F.

9. The integrated process of claim 7 wherein the pressure is from 250 psig to 600 psig.

10. The integrated process of claim 1 wherein the second portion of the natural gas is also pre-treated to separate at least a portion of the $CO_2$ therefrom.

11. The integrated process of claim 1 wherein all of the natural gas employed in the integrated process is initially pre-treated to remove $CO_2$ therefrom, and the second portion of the natural gas is a portion of the natural gas feed resulting from pre-treatment of the natural gas.

12. An integrated process for producing LNG products in a LNG Phase production zone and conversion of natural gas into GTL products that include methanol in a GTL Phase production zone from a natural gas comprising hydrocarbons and $CO_2$, the process comprising the steps of:
pre-treating at least a first portion of the natural gas to separate at least a portion of the $CO_2$ therefrom and produce a natural gas feed having reduced $CO_2$ content and a stream rich in $CO_2$;
converting the natural gas feed into at least one natural gas vapor component and an LNG product in the LNG Phase;
converting the at least one natural gas vapor component, and optionally a second portion of the natural gas, to a synthesis gas by steam methane reformation; and
reacting the stream rich in $CO_2$ with at least a portion of the synthesis gas in the GTL Phase to produce methanol.

13. The integrated process of claim 12 wherein a second portion of the natural gas is converted to synthesis gas.

14. The integrated process of claim 13 wherein the second portion of the natural gas is pre-treated to separate at least a portion of the $CO_2$ therefrom.

15. The integrated process of claim 13 wherein all of the natural gas employed in the integrated process is initially pre-treated to remove $CO_2$ therefrom, and the second portion of the natural gas is a portion of the natural gas feed resulting from pre-treatment of the natural gas.

16. The integrated process of claim 12 wherein:
conversion of the at least one natural gas vapor component and optional second portion of the natural gas to synthesis gas further comprises:
a pre-reforming step for reducing the molar concentration of ethane and higher boiling point hydrocarbon in the at least one natural gas vapor component and optional second portion of the natural gas to produce a pre-reformed natural gas vapor; and
a reforming step for converting at least a portion of the pre-reformed natural gas vapor to synthesis gas;
the reacting step further comprises:
reacting at least a portion of the synthesis gas and the stream rich in $CO_2$ to produce methanol, optionally at least one other GTL product, and a stream of unconverted synthesis gas; and a recycling step is employed wherein at least a portion of the stream of unconverted synthesis gas is recycled to either the pre-reforming step or the reforming step, wherein at least a portion of the at least one natural gas vapor component is directed to at least one step selected from the pre-reforming step, the reforming step, or the recycling step.

17. The integrated process of claim 16 further comprising feeding the stream rich in $CO_2$ with the one or more of the expansion/separation cycle natural gas vapor components such that the stream rich in $CO_2$ is mixed with the vapor components prior to the pre-reforming step.

18. The integrated process of claim 16 further comprising feeding the stream rich in $CO_2$ with the pre-reformed natural gas vapor such that the stream rich in $CO_2$ is mixed with the gas vapor prior to the reforming step.

19. The integrated process of claim 16 wherein the recycling step comprises a compression step for recycling the stream of unconverted synthesis gas and the one or more of the natural gas vapor components is added upstream of the compression step.

20. The integrated process of claim 16 wherein at least a portion of the optional GTL product is at least one member selected from the group consisting of products of a Fischer Tropsch reaction, dimethyl ether, and hydrogen.

21. The integrated process of claim 12 wherein conversion of the natural gas feed in the LNG Phase comprises the steps of:
   cooling the natural gas feed in at least one cooling step so as to provide a cooled natural gas stream;
   processing the cooled natural gas stream in at least two expansion/separation cycles, each expansion/separation cycle comprising the substeps of:
   a. isentropically or isenthalpically expanding at least a portion of the cooled natural gas steam and producing a natural gas vapor component and a LNG component;
   b. separating at least a portion of the natural gas vapor component from the LNG component; and
   c. repeating substeps a. through b.,
   wherein at least a portion of the LNG component from the previous expansion/separation cycle is directed to each successive Substep a., and
   wherein the LNG product is the LNG component after the final separating step and is substantially liquid at substantially atmospheric pressure.

22. The integrated process of claim 21 further comprising feeding the stream rich in $CO_2$ with the one or more of the expansion/separation cycle natural gas vapor components such that the stream rich in $CO_2$ is mixed with the vapor components prior to formation of the synthesis gas.

23. The integrated process of claim 21 wherein each of the expansion/separation cycles comprise an isenthalpic expansion of the cooled natural gas streams and the LNG components across a Joule Thompson valve wherein the pressure of the cooled natural gas stream and each successive LNG component are each reduced by at least 15 psig.

24. The integrated process of claim 21 wherein the first expansion/separation cycle comprises reducing the pressure of the cooled natural gas stream by at least 30 psig and reducing the temperature of such cooled natural gas stream by at least 10° F.

25. The integrated process of claim 21 wherein the expanded pressure of the natural gas vapor component and the LNG component from the first expansion/separation cycle step is not less than 75 psia.

26. The integrated process of claim 12 wherein conversion of the natural gas feed in the LNG Phase comprises the steps of:
   cooling the natural gas feed in at least one cooling step so as to provide a cooled natural gas stream;
   isentropically or isenthalpically expanding at least a portion of the cooled natural gas steam in a first expansion step and producing a first natural gas vapor component and a first LNG component;
   separating at least a portion of the first natural gas vapor component from the first LNG component;
   isentropically or isenthalpically expanding at least a portion of the first LNG component in a second expansion step and producing a second natural gas vapor component and a second LNG component; and
   separating at least a portion of the second natural gas vapor component from the second LNG component,
   wherein the LNG product is the LNG component after the final separating step and is substantially liquid at substantially atmospheric pressure.

27. The integrated process of claim 26 further comprising feeding the stream rich in $CO_2$ with the one or more of the expansion/separation cycle natural gas vapor components such that the stream rich in $CO_2$ is mixed with the vapor components prior to formation of the synthesis gas.

28. The integrated process of claim 26 wherein the first and second expansion steps each comprise an isenthalpic expansion of the cooled natural gas stream and the first LNG component across a Joule Thompson valve wherein the pressure of the cooled natural gas stream and the first LNG component are each reduced by at least 15 psig.

29. The integrated process of claim 26 wherein the first expansion step comprises reducing the pressure of such cooled natural gas stream by at least 30 psig and reducing the temperature of such cooled natural gas stream by at least 10° F.

30. The integrated process of claim 26 wherein the first natural gas component comprises a higher mole percent of nitrogen and a lower mole percent of ethane and all higher boiling point hydrocarbon than the cooled natural gas stream.

31. The integrated process of claim 26 wherein the expanded pressure of the first expansion step is not less than 75 psia.

32. The integrated process of claim 26 wherein at least a portion of the first natural gas vapor component becomes a fuel source for at least one member selected from the group consisting of a LNG refrigeration compressor and the reforming step.

33. The integrated process of claim 12 wherein conversion of the natural gas feed in the LNG Phase comprises the steps of:
   cooling the natural gas feed in at least one cooling step so as to provide a cooled natural gas stream;
   isentropically or isenthalpically expanding at least a portion of the cooled natural gas steam in a first autorefrigeration step and producing a first natural gas vapor component and a first LNG component;
   separating at least a portion of the first natural gas vapor component from the first LNG component;
   isentropically or isenthalpically expanding at least a portion of the first LNG component in a second autorefrigeration step and producing a second natural gas vapor component and a second LNG component;

separating at least a portion of the second natural gas vapor component from the second LNG component; and compressing at least a portion of one or more of the first and second natural gas vapor components and producing a compressed natural gas feedstock having a higher temperature than either of the first and second natural gas vapor components, wherein the LNG product is the second LNG component and is substantially liquid at substantially atmospheric pressure.

34. The integrated process of claim 33 further comprising feeding the stream rich in $CO_2$ into the one or more of the natural gas vapor components such that the stream rich in $CO_2$ is commingled with the vapor components prior to formation of the synthesis gas.

35. The integrated process of claim 33 wherein the expanded pressure of the first expansion step is not less than 75 psia.

36. The integrated process of claim 33 wherein:
the temperature of the cooled natural gas stream is not more than $-20°$ F.;
the temperature of the cooled natural gas stream is reduced by at least $3°$ F. in the first autorefrigeration step; and
the temperature of the second natural gas vapor component is at least $3°$ F. below that of the first LNG component.

37. The integrated process of claim 33 wherein the first and second autorefrigeration steps each comprise an isenthalpic expansion of the cooled natural gas stream and the first LNG component across a Joule Thompson valve wherein the pressure of the cooled natural gas stream and the first LNG component are each reduced by at least 15 psig.

38. The integrated process of claim 33 wherein the first autorefrigeration step comprises reducing the pressure of such cooled natural gas stream by at least 30 psig and reducing the temperature of such cooled natural gas stream by at least $10°$ F.

39. The integrated process of claim 33 wherein:
conversion of the at least one natural gas vapor component and optional second portion of the natural gas to synthesis gas further comprises:
a pre-reforming step for reducing the molar concentration of ethane and higher boiling point hydrocarbon of the compressed natural gas feedstock and producing a pre-reformed natural gas feedstock; and
a reforming step for converting at least a portion of the pre-reformed natural gas feedstock to synthesis gas;
the reacting step further comprises:
a conversion step wherein at least a portion of the synthesis gas and the stream rich in $CO_2$ are reacted to produce methanol and a stream of unconverted synthesis gas, and at least one other reaction step selected from conversion of the synthesis gas to (i) hydrogen, (ii) dimethyl ether, or (iii) a product of a Fischer Tropsch reaction, the other reaction step converting the synthesis gas into the GTL product and a stream of unconverted synthesis gas; and
a recycling step is employed wherein at least a portion of the stream of unconverted synthesis gas is recycled to either the pre-reforming step or the reforming step, wherein at least a portion of the compressed natural gas feedstock is directed to at least one step selected from the pre-reforming step, the reforming step, or the recycling step.

40. The integrated process of claim 39 further comprising feeding the stream rich in $CO_2$ with the compressed natural gas feedstock such that the stream rich in $CO_2$ is mixed with the feedstock prior to the pre-reforming step.

41. The integrated process of claim 39 further comprising feeding the stream rich in $CO_2$ with the pre-reformed natural gas feedstock such that the stream rich in $CO_2$ is mixed with the feedstock prior to the reforming step.

42. The integrated process of claim 12 wherein conversion of the natural gas feed in the LNG Phase comprises the steps of:
cooling the natural gas feed in at least one cooling step so as to provide a cooled natural gas stream;
isentropically or isenthalpically expanding at least a portion of the cooled natural gas steam in a first autorefrigeration step and producing a first natural gas vapor component and a first LNG component;
separating at least a portion of the first natural gas vapor component from the first LNG component;
isentropically or isenthalpically expanding at least a portion of the first LNG component in a second autorefrigeration step and producing a second natural gas vapor component and a second LNG component;
separating at least a portion of the second natural gas vapor component from the second LNG component;
isentropically or isenthalpically expanding at least a portion of the second LNG component in a third autorefrigeration step and producing a third natural gas vapor component and a LNG product; and
separating at least a portion of the third natural gas vapor component from the LNG product.

43. The integrated process of claim 42 further comprising feeding the stream rich in $CO_2$ with the one or more of the natural gas vapor components such that the stream rich in $CO_2$ is mixed with the vapor components prior to formation of the synthesis gas.

44. The integrated process of claim 42 wherein the LNG product is substantially liquid at substantially atmospheric pressure.

45. The integrated process of claim 42 wherein the portion of one or more of the first, second and third natural gas vapor components is compressed producing a compressed GTL feedstock having a higher temperature than any of the first, second and third natural gas vapor components exiting the first, second and third autorefrigeration steps.

46. The integrated process of claim 42 wherein at least a portion of either or both of the first or second natural gas vapor components is converted into GTL product and at least a portion of the third natural gas vapor is compressed, refrigerated and directed to any one or more of the cooled natural gas stream, the first LNG component, the second LNG component, or the LNG product.

* * * * *